(12) United States Patent
Hayashi et al.

(10) Patent No.: US 10,136,809 B2
(45) Date of Patent: Nov. 27, 2018

(54) OPHTHALMIC APPARATUS

(71) Applicant: KABUSHIKI KAISHA TOPCON, Tokyo (JP)

(72) Inventors: Takefumi Hayashi, Wako (JP); Shunichi Morishima, Kawaguchi (JP); Yoko Tatara, Tokyo (JP)

(73) Assignee: KABUSHIKI KAISHA TOPCON, Itabashi-ku, Tokyo (JP)

( * ) Notice: Subject to any disclaimer, the term of this patent is extended or adjusted under 35 U.S.C. 154(b) by 0 days.

(21) Appl. No.: 15/519,688

(22) PCT Filed: Oct. 7, 2015

(86) PCT No.: PCT/JP2015/078438
§ 371 (c)(1),
(2) Date: Apr. 17, 2017

(87) PCT Pub. No.: WO2016/063722
PCT Pub. Date: Apr. 28, 2016

(65) Prior Publication Data
US 2017/0245756 A1     Aug. 31, 2017

(30) Foreign Application Priority Data

Oct. 22, 2014   (JP) ................................ 2014-215049

(51) Int. Cl.
*A61B 3/103*   (2006.01)
*A61B 3/028*   (2006.01)
(Continued)

(52) U.S. Cl.
CPC ............ *A61B 3/103* (2013.01); *A61B 3/0025* (2013.01); *A61B 3/028* (2013.01); *A61B 3/036* (2013.01);
(Continued)

(58) Field of Classification Search
CPC ........... A61B 3/0008; A61B 3/14; A61B 3/12; A61B 3/102; A61B 3/0025
(Continued)

(56) References Cited

U.S. PATENT DOCUMENTS 5,523,809 A   6/1996  Kohayakawa
5,751,396 A   5/1998  Masuda et al.
(Continued)

FOREIGN PATENT DOCUMENTS

EP   1602320 A1   7/2005
EP   1602320 A1   12/2005
(Continued)

OTHER PUBLICATIONS

International Search Report and Written Opinion dated Apr. 28, 2016 in connection with International Patent Application No. PCT/JP2015/078438, 7 pgs.
(Continued)

*Primary Examiner* — Mohammed Hasan
(74) *Attorney, Agent, or Firm* — Chiesa Shahinian & Giantomasi PC

(57) ABSTRACT

A technology for achieving a reduction in size of an ophthalmic apparatus capable of performing a plurality of kinds of measurements performed before cataract surgery is provided. An ophthalmic apparatus is described that includes a refractive power measurement unit and an eyeball information measurement unit. The refractive power measurement unit is configured to project light from a light source onto a subject's eye and detect returning light thereof to determine refractive power of an ocular optical system of the subject's eye. The eyeball information measurement unit is configured to project light from the same light source onto the
(Continued)

subject's eye and detect returning light thereof to determine eyeball information representing structure of the subject's eye.

20 Claims, 12 Drawing Sheets

(51) Int. Cl.
    *A61B 3/10* (2006.01)
    *A61B 3/107* (2006.01)
    *A61B 3/036* (2006.01)
    *A61B 3/00* (2006.01)
    *A61B 3/06* (2006.01)

(52) U.S. Cl.
    CPC .............. *A61B 3/10* (2013.01); *A61B 3/1005* (2013.01); *A61B 3/107* (2013.01); *A61B 3/063* (2013.01); *A61B 3/102* (2013.01)

(58) Field of Classification Search
    USPC .................................................. 351/200–246
    See application file for complete search history.

(56) References Cited

U.S. PATENT DOCUMENTS

| | | |
|---|---|---|
| 2007/0279592 A1 | 12/2007 | Hanebuchi |
| 2011/0075097 A1 | 3/2011 | Hamaguchi et al. |
| 2011/0187996 A1* | 8/2011 | Ueno ..................... A61B 3/103 351/239 |
| 2012/0197102 A1 | 8/2012 | Hanebuchi et al. |
| 2013/0135582 A1 | 5/2013 | Hanebuchi et al. |
| 2013/0229627 A1 | 9/2013 | Kato et al. |
| 2014/0347630 A1 | 11/2014 | Foggi et al. |
| 2015/0320308 A1* | 11/2015 | Akiba ..................... A61B 3/102 382/131 |

FOREIGN PATENT DOCUMENTS

| | | |
|---|---|---|
| EP | 1738680 A1 | 1/2007 |
| EP | 2415393 A1 | 8/2011 |
| JP | H05-154103 A | 6/1993 |
| JP | H06-121773 A | 5/1994 |
| JP | 2005-342204 A | 12/2005 |
| JP | 4523338 B2 | 8/2010 |
| JP | 201234788 A | 2/2012 |
| JP | 2012152469 A | 8/2012 |
| JP | 2013-135837 A | 7/2013 |
| JP | 2013-180111 A | 9/2013 |
| JP | 5500587 B2 | 5/2014 |
| JP | 2014-128306 A | 7/2014 |
| WO | 2013111090 A1 | 8/2013 |

OTHER PUBLICATIONS

Extended Search Report dated Jun. 19, 2018, in connection with European Patent Application No. 15851843.1, 23 pgs.

* cited by examiner

OPHTHALMIC APPARATUS

CROSS-REFERENCE TO RELATED APPLICATIONS

This application is a U.S. national phase filing under 35 U.S.C. § 371 of PCT Application No. PCT/JP2015/078438, filed Oct. 7, 2015, and claims priority thereto under 35 U.S.C. § 119 to Japanese Patent Application No. 2014-215049, filed Oct. 22, 2014, the entireties of both of which are incorporated by reference herein.

FIELD

Embodiments described herein relate generally to an ophthalmic apparatus.

BACKGROUND

Cataract is an ocular disease whose visual acuity gradually decreases as the crystalline lens that plays the role of a lens becomes cloudy. In general, cataract surgery is performed on a subject's eye with cataract. For example, in cataract surgery, a cloudy lens is removed and an intraocular lens (IOL, hereinafter) is inserted instead. Types of IOLs include those having only the spherical power, toric IOLs capable of correcting astigmatism, and multifocal IOLs that can focus on both far distance and near distance. Prior to cataract surgery, it is necessary to measure eyeball information representing the structure of the subject's eye such as axial length and corneal curvature radius with an ophthalmic apparatus, and determine the power of an IOL from the eyeball information measured.

Such ophthalmic apparatuses are disclosed in, for example, Japanese Patent No. 4523338, Japanese Patent No. 5500587, Japanese Unexamined Patent Application Publication No. 2013-180111 and International Publication WO2013/111090. Japanese Patent No. 452338 discloses an ophthalmic apparatus that includes an optical system for measuring the axial length and an optical system for measuring the refractive power of the subject's eye and is capable of simultaneously performing the measurement of the axial length and the measurement of the refractive power of the subject's eye. Japanese Patent No. 5500587 discloses an ophthalmic apparatus including an optical system for measuring the axial length and an optical system for measuring the shape of the cornea. Japanese Unexamined Patent Application Publication No. 2013-180111 discloses an ophthalmic apparatus capable of measuring the axial length using a technology of swept source optical coherence tomography (OCT, hereinafter). International Publication WO2013/111090 discloses a method of measuring the axial length using a Michelson interferometer.

SUMMARY

However, in the conventional technology, a plurality of ophthalmic apparatuses is necessarily used before cataract surgery, and thus the installation space for those apparatuses must be secured. On the other hand, a single ophthalmic apparatus capable of acquiring a plurality of kinds of eyeball information is large in size.

In order to solve the aforementioned problems, the object of the present invention is to provide a technology for achieving a reduction in size of an ophthalmic apparatus capable of performing a plurality of kinds of measurements performed before cataract surgery.

An ophthalmic apparatus of an embodiment includes a refractive power measurement unit and an eyeball information measurement unit. The refractive power measurement unit is configured to project light from a light source onto a subject's eye and detect returning light thereof to determine refractive power of an ocular optical system of the subject's eye. The eyeball information measurement unit is configured to project light from the same light source onto the subject's eye and detect returning light thereof to determine eyeball information representing structure of the subject's eye.

According to the embodiments, it is possible to reduce the size of an ophthalmic apparatus capable of performing a plurality of kinds of measurements performed before cataract surgery.

DETAILED DESCRIPTION

The ophthalmic apparatus according to the first embodiment is capable of performing objective measurement and subjective measurement with a single apparatus. The objective measurement is to acquire information on the subject's eye mainly by the use of a physical method without referring to the responses from the subject. The objective measurement includes objective measurement for measuring a value(s) related to the subject's eye and an imaging for acquiring an image of the subject's eye. Examples of the objective measurement include objective refractometry, corneal shape measurement, tonometry, fundus imaging, OCT measurement employing the OCT method, and the like. The subjective measurement is to acquire the result based on the responses from the subject. Examples of the subjective measurement include a visual field test, and subjective refractometry such as a far vision test, a near vision test, a contrast test, a glare test and the like. In subjective measurement, information (such as a visual target(s)) is presented to a subject, and a result is acquired based on the subject's response(s) to the information.

In the present embodiment, the case of using the Fourier domain OCT method in the OCT measurement will be described. In particular, the ophthalmic apparatus according to the embodiment can perform OCT measurement using the spectral domain OCT method. For the OCT measurement, a type other than the spectral domain (for example, a swept source OCT method) may be used. The time domain OCT method may be employed in the OCT measurement of the present embodiment.

Further, the ophthalmic apparatus according to the embodiment can perform at least any one of an arbitrary kind of subjective measurement and an arbitrary kind of objective measurement. Hereinafter, a case is considered in which the ophthalmic apparatus according to the embodiment is capable of performing the far vision test, the near vision test, the contrast test, the glare test and the like as the subjective measurement, and is also capable of performing the objective refractometry, the corneal shape measurement, the OCT measurement and the like as the objective measurement. The OCT measurement is performed to acquire eyeball information representing the structure of the subject's eye such as the axial length, the corneal thickness, the anterior chamber depth, and the crystalline lens thickness. In the embodiment, it is assumed that the eyeball information includes an intraocular distance indicating a distance between predetermined two portions in the eye such as the axial length and the crystalline lens thickness. However, the configuration of the ophthalmic apparatus according to the embodiment is not limited to this.

(External Configuration of Ophthalmic Apparatus)

Figure 1:
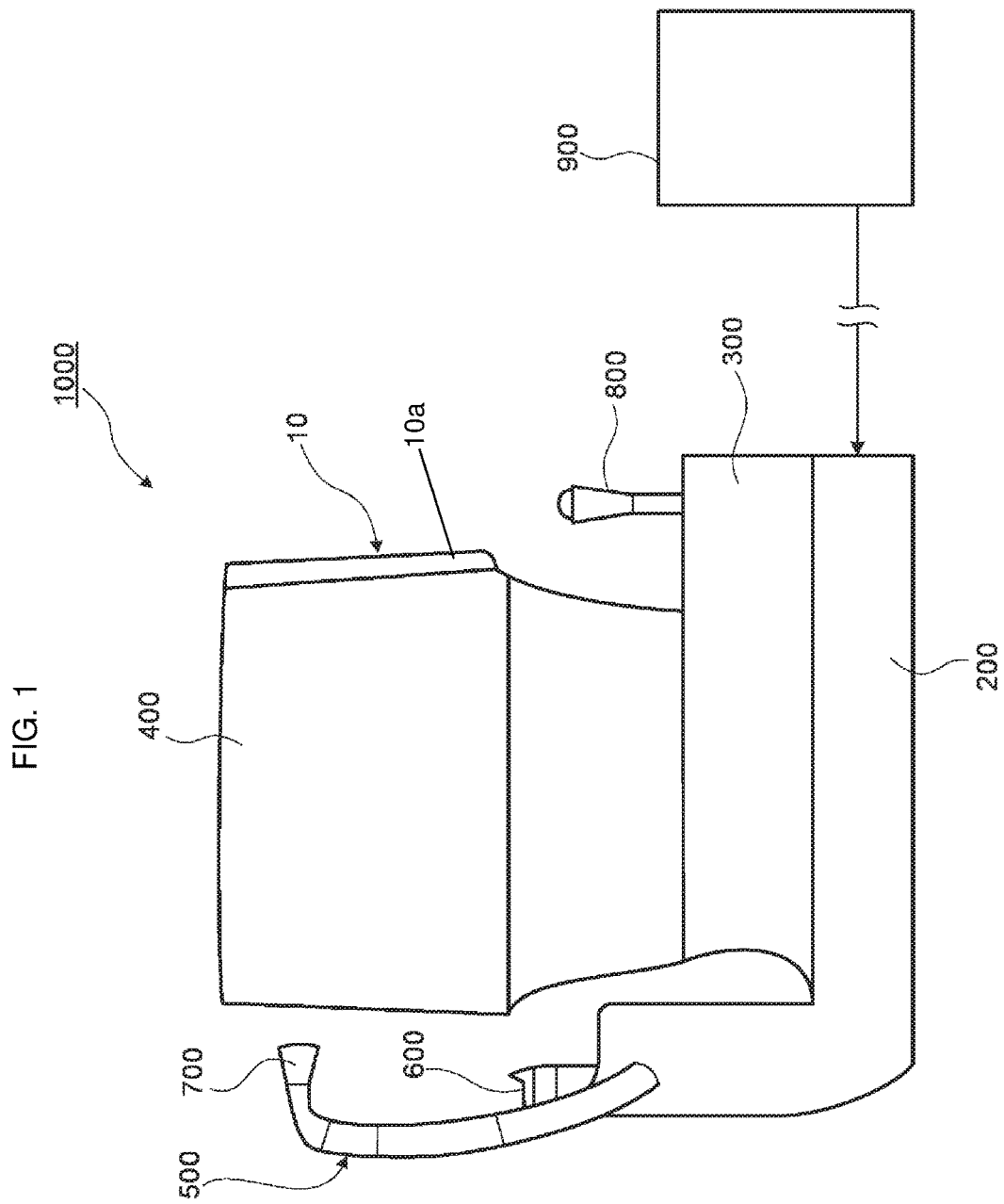
FIG. 1 is a schematic diagram illustrating an example of the configuration of an ophthalmic apparatus according to an embodiment.

FIG. 1 shows an external configuration of the ophthalmic apparatus according to the first embodiment. An ophthalmic apparatus 1000 includes a base 200, a frame 300, a head unit 400, a face support 500, a joystick 800, and a display unit 10.

The frame 300 is movable in the front-back direction and in the lateral direction with respect to the base 200. The head unit 400 is formed integrally with the frame 300. The face support 500 is formed integrally with the base 200.

The face support 500 includes a chin rest 600 and a forehead rest 700. The face support 500 holds the face of the subject (not shown). For example, the examiner is located on the opposite side of the subject from the ophthalmic apparatus 1000 and conducts a test. The joystick 800 and the display unit 10 are arranged at positions on the examiner's side. The joystick 800 is provided on the frame 300. The display unit 10 is provided on the surface of the head unit 400 on the examiner's side. The display unit 10 is, for example, a flat panel display such as a liquid crystal display. The display unit 10 has display screen 10a of a touch panel type.

The head unit 400 is movable in the front-back direction and in the lateral direction in accordance with the tilting operation of the joystick 800. Further, the head unit 400 is movable in the vertical direction in accordance with the operation of rotating the joystick 800 around the axis of the joystick 800. Through these operations, the position of the head unit 400 is adjusted with respect to the face of the subject held by the face support 500. The movement of the head unit 400 in the lateral direction is also performed, for example, to switch a subject's eye tested by the ophthalmic apparatus 1000 from the left eye to the right eye or from the right eye to the left eye.

An external device 900 is connected to the ophthalmic apparatus 1000. The external device 900 may be an arbitrary kind of device. In addition, a connection mode (a communication mode or the like) between the ophthalmic apparatus 1000 and the external device 900 may also be arbitrary. The external device 900 includes, for example, a spectacle lens measurement device for measuring optical properties of a lens. The spectacle lens measurement device measures the power of the spectacle lens worn by the subject and inputs the measurement data to the ophthalmic apparatus 1000. The external device 900 may be any other kind of ophthalmic apparatus. The external device 900 may be an apparatus having a function of reading information from a recording medium (i.e., a reader), or an apparatus having a function of writing information on a recording medium (i.e., a writer).

Another example of the external device 900 includes a computer used in the medical institution. Examples of such an in-hospital computer include a Hospital Information System (HIS) server, a Digital Imaging and Communications in Medicine (DICOM) server, a doctor's terminal, and the like. The external device 900 may include a computer used outside the medical institution. Examples of such an out-of-hospital computer include a mobile terminal, a personal terminal, a server or terminal of the manufacturer of the ophthalmic apparatus 1000, a cloud server, and the like.

(Configuration of Optical System)

The ophthalmic apparatus 1000 includes an optical system for examining a subject's eye. An example of the configuration of the optical system will be described with reference to FIG. 2 to FIG. 5B. The optical system is provided in the head unit 400. The optical system includes an observation system 5, a fixation and subjective measurement system 4, a glare light projection system 8, a refractometry light projection system 6, a refractometry light reception system 7, a Z alignment projection system 1, an XY alignment spot projection system 2, a keratometry ring projection system 3, and an interference optical system 14. A processor 9 performs various kinds of processes.

The observation system 5 is an optical system for observing the anterior segment of the subject's eye E. The fixation and subjective measurement system 4 is an optical system for presenting a fixation target(s) and a visual target(s) for subjective measurement to the subject's eye E. The glare light projection system 8 is an optical system for projecting glare light onto the subject's eye together with the aforementioned visual target(s). The refractometry light projection system 6 is an optical system for projecting a light beam for objectively measuring the eye refractive power onto the subject's eye. The refractometry light reception system 7 is an optical system for receiving fundus reflection light of the light projected onto the subject's eye by the refractometry light projection system 6. The refractometry light reception system 7 has a function of forming a plurality of point-like light beams from returning light (reflected light, reflected light beam) from the fundus Ef of measurement light output from the light source (common) in the interference optical system 14, and of detecting the images formed by the plurality of point-like light beams. The fixation and subjective measurement system 4 is an optical system for performing subjective measurement. The fixation and subjective measurement system 4 of the present example has a function of presenting the visual target(s) to the subject's eye E. The Z alignment projection system 1 and the XY alignment spot projection system 2 are optical systems for projecting light used to perform alignment (XYZ alignment) of the optical system with respect to the subject's eye E. The Z alignment projection system 1 has a function of performing alignment in a direction along the optical axis of the observation system 5 (that is, alignment in the front-back direction). The XY alignment spot projection system 2 has a function of projecting a spot for performing alignment in a direction perpendicular to the optical axis of the observation system 5 (that is, alignment in the vertical direction and the lateral direction). The interference optical system 14 is an optical system for projecting the measurement light onto the fundus Ef and performing OCT measurement to carry out the objective measurement. The interference optical system 14 has a function of projecting the measurement light output from a light source 141 onto the fundus Ef and a function of detecting returning light of the measurement light.

(Observation System 5)

The observation system 5 includes an objective lens 51, a dichroic mirror 52, a diaphragm 53, a half mirror 54, relay lenses 55 and 56, an imaging lens 57, and an image pickup device (CCD) 58. The output of the image pickup device 58 is input to the processor 9. The processor 9 controls the display unit 10 to display an anterior segment image E' based on the signal input from the image pickup device 58.

Between the objective lens 51 and the subject's eye E, a keratometry plate 31 is provided. The keratometry plate 31 is used to project a ring-shaped light beam for measuring the shape of the cornea onto the cornea C of the subject's eye E.

(Z Alignment Projection System 1 and XY Alignment Spot Projection System 2)

The Z alignment projection system 1 is provided in the vicinity of the keratometry plate 31. As described above, the Z alignment projection system 1 is used for alignment in the front-back direction along the optical axis of the observation system 5. The Z alignment projection system 1 has a Z alignment light source 11. Light emitted from the Z alignment light source 11 is projected onto the cornea C. The light projected onto the cornea C is reflected by the cornea C and is projected onto a line sensor 13 via an imaging lens 12. When the position of the vertex of the cornea varies in the front-back direction with respect to the optical axis of the observation system 5, the position of the light beam projected onto the line sensor 13 changes. By analyzing the change in the projection position, it is possible to measure the position of the vertex of the cornea of the subject's eye E with respect to the objective lens 51, and to perform alignment based on the measured value.

The XY alignment spot projection system 2 forms an optical path branched from the observation system 5 via the half mirror 54. As described above, the XY alignment spot projection system 2 is used for alignment in the vertical direction and in the lateral direction. The XY alignment spot projection system 2 has an XY alignment light source 21. Part of the light output from the XY alignment light source 21 is reflected by the half mirror 54, passes through the diaphragm 53, transmits through the dichroic mirror 52, passes through the objective lens 51, and is projected onto the subject's eye E. The light projected onto the subject's eye E is reflected by the cornea C, passes through the objective lens 51, and is projected onto the image pickup device 58 through the same optical path as the observation system 5.

Figure 2A:
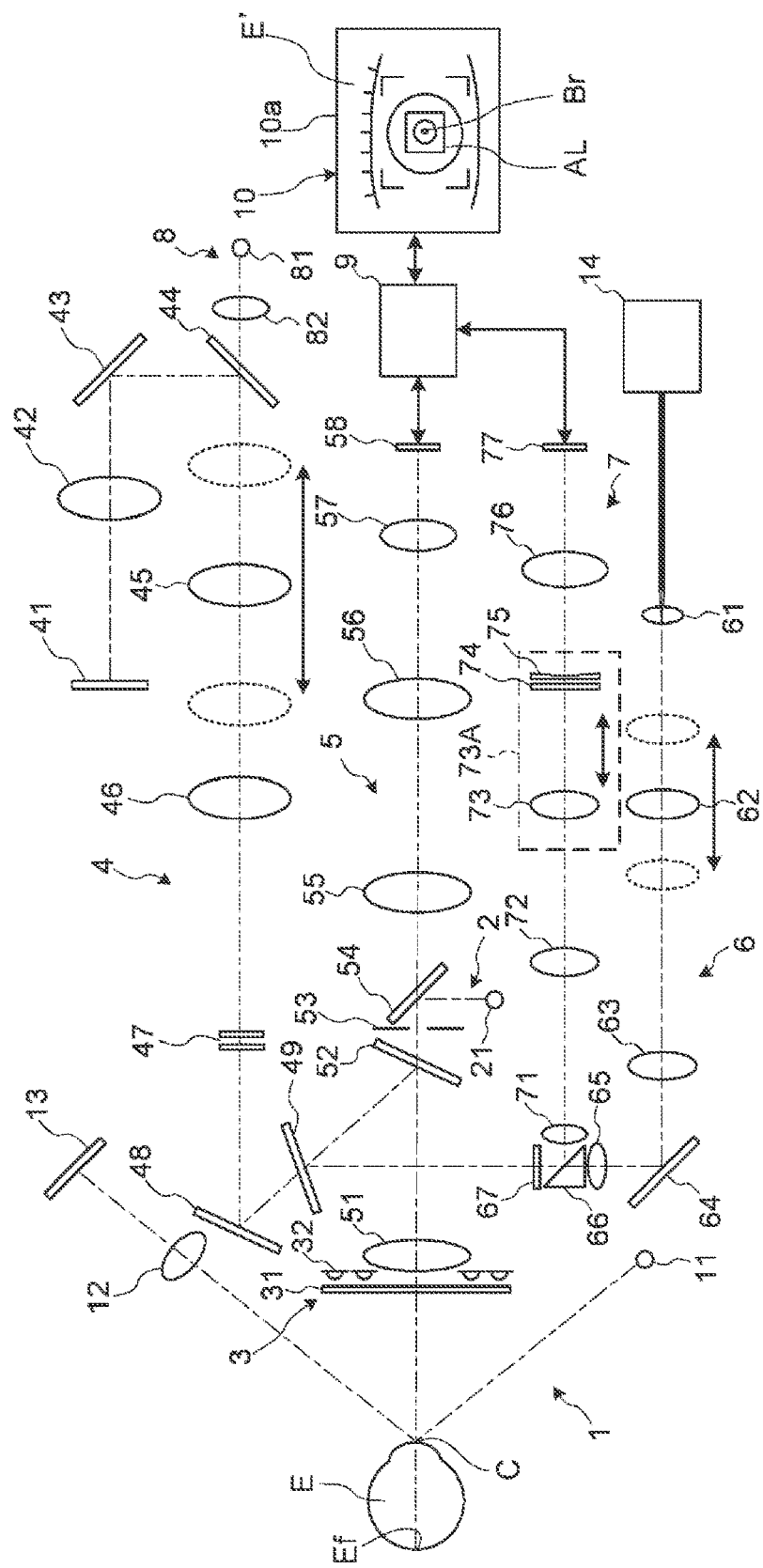
FIG. 2A is a schematic diagram illustrating an example of the configuration of the ophthalmic apparatus according to the embodiment.

As shown in FIG. 2 and the like, an alignment mark AL and a bright spot image Br that is reflection from the cornea C are displayed together with the anterior segment image E' on the display screen 10a. When manual alignment is performed, the user adjusts the position of the head unit 400 by operating the joystick 800 while referring to the information displayed on the display screen 10a, for example. At this time, for example, the processor 9 calculates the amount of deviation in the vertical and lateral directions based on the amount of deviation between the alignment mark AL and the bright spot image Br. In addition, based on the processing information from the Z alignment projection system 1, the processor 9 may control the display screen 10a to display the amount of deviation in the direction along the optical axis. The processor 9 can perform control to commence the measurement in response to the completion of the alignment.

In the case of automatic alignment, the ophthalmic apparatus controls an electric mechanism to move the head unit 400 so that the aforementioned amount of deviation is eliminated. The electric mechanism includes an actuator configured to generate a driving force and a member configured to transmit the driving force to the head unit 400. The processor 9 can perform control to commence the measurement in response to the completion of the alignment.

(Fixation and Subjective Measurement System 4)

The fixation and subjective measurement system 4 includes a self-luminous liquid crystal panel 41, a relay lens 42, a reflection mirror 43, a half mirror 44, a focusing lens 45, a relay lens 46, a variable cross cylinder (hereinafter, VCC) lens 47, a reflection mirror 48, dichroic mirrors 49 and 52, and the objective lens 51.

The glare light projection system 8 includes a glare light source 81 that emits glare light to be projected onto the subject's eye E and a relay lens 82. The glare light source 81, the relay lens 82, the half mirror 44, the focusing lens 45, the relay lens 46, the VCC lens 47, the reflection mirror 48, the dichroic mirrors 49 and 52, and the objective lens 51 constitute the glare light projection system 8. The glare light projection system 8 projects the glare light onto the subject's eye E in parallel to the projection of the visual target(s) performed by the fixation and subjective measurement system 4.

The fixation and subjective measurement system 4 is capable of projecting the visual target(s) for a visual acuity measurement on the fundus Ef of the subject's eye E. Further, the fixation and subjective measurement system 4 can change the contrast of the visual target(s).

In the objective measurement (objective refractometry, etc.), a landscape chart is projected on the fundus Ef. Alignment is performed while causing the subject to gaze at the landscape chart, and then the refractive power is measured in a fogged visual state.

The fixation and subjective measurement system 4 may be configured to include an optical chart to project a visual target(s) for a visual acuity measurement on the fundus Ef.

(Refractometry Light Projection System 6 and Refractometry Light Reception System 7)

The refractometry light projection system 6 and the refractometry light reception system 7 constitute a refractometry system. The refractometry light projection system 6 has a function of projecting light emitted from the light source 141 of the interference optical system 14 onto the fundus Ef of the subject's eye E. The light emitted from the light source 141 passes through a fiber coupler 142 and becomes a parallel light beam by a collimator lens 61, and then travels through a focusing lens 62, a relay lens 63, a reflection mirror 64, a pupil lens 65, the central portion of a perforated prism 66. Further, the light is decentered by a light beam decentered prism (eccentric prism) 67 with a rotation mechanism that can be inserted into and removed from the optical path. Then, the light is reflected by the dichroic mirrors 49 and 52, passes through the objective lens 51, and is projected onto the fundus Ef of the subject's eye E. The light beam decentered prism (eccentric prism) 67 corresponds to a decentered member. Here, etching has been applied to the surface of the pupil lens 65, which is disposed near the position conjugate with the pupil of the subject's eye E, so that only the central portion of the pupil lens 65 transmits light. The effect of the decentered prism 67 functions to reduce deterioration of the accuracy of the measurement due to the change of or the decrease of the light amount distribution of the measurement light when overlap occurs between the projection area of the measurement light beam and a blood vessel or a lesion site in the fundus Ef of the subject's eye E. Rotation of the decentered prism 67 averages the degree of the overlap between the measurement light beam and the blood vessel or the lesion site. With this, the accuracy of measurement can be improved. Further, since the pupil lens 65 is disposed near the position conjugate with the pupil of the subject's eye E, when the decentered prism 67 is rotated, the center of the light beam becomes decentered with respect to the pupil center of the subject's eye E. This makes it possible for the measurement light to pass through the pupil even when the pupil of the subject's eye E is small. However, even if the pupil lens 65 is arranged at a conjugate position with the pupil, the effect of improving the accuracy of the measurement can be obtained. This means that the position of the pupil lens 65 is selectable in accordance with the specification of the apparatus. The center of the light beam that has passed through the perforated prism 66 and the decentered prism 67 is decentered and is projected onto the fundus Ef from a position apart from the pupil of the subject's eye E by a predetermined distance. As will be described later, however, the light beam reflected from the fundus Ef returns to the decentered prism 67 of the same optical path, so that the state becomes as if the decentered prism 67 does not exist, and the light beam is projected onto an image pickup device 77 by the refractometry light reception system 7.

Figure 2B:
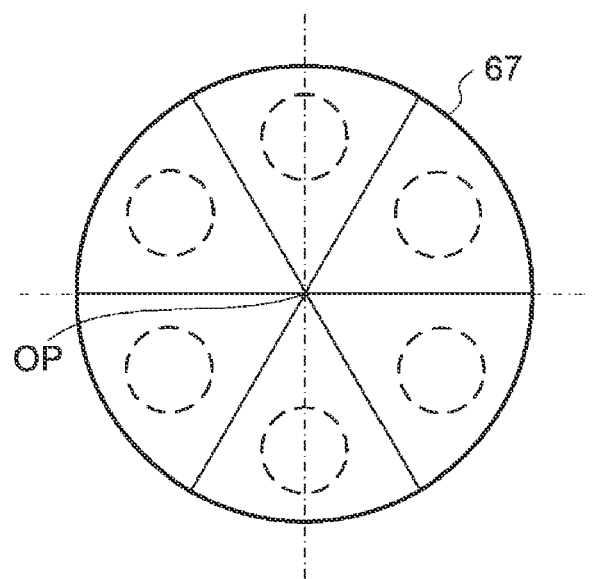
FIG. 2B is a schematic diagram illustrating an example of the configuration of the ophthalmic apparatus according to the embodiment.
Figure 2C:
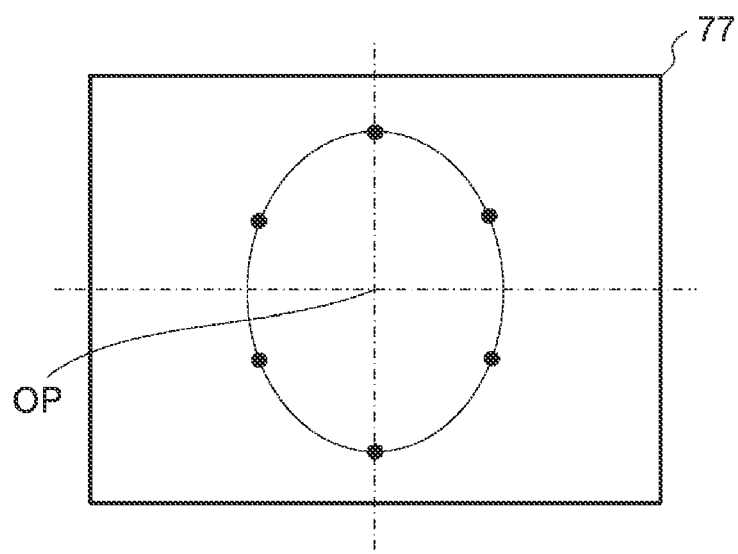
FIG. 2C is a schematic diagram illustrating an example of the configuration of the ophthalmic apparatus according to the embodiment.
Figure 3:
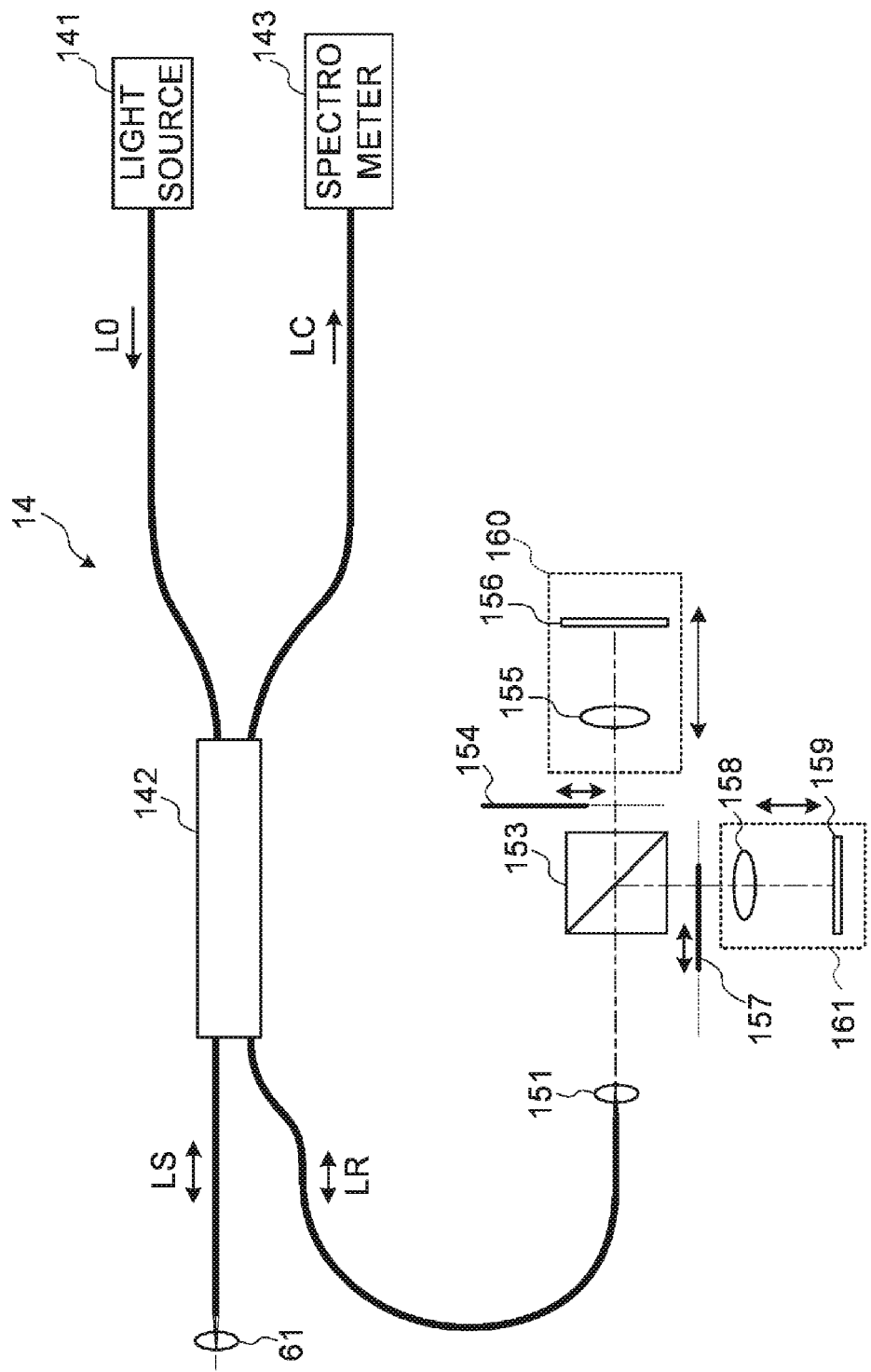
FIG. 3 is a schematic diagram illustrating an example of the configuration of the ophthalmic apparatus according to the embodiment.

In the refractometry light reception system 7, the light reflected from the fundus Ef is reflected by the objective lens 51, and the dichroic mirrors 52 and 49, is decentered by the decentered prism 67, and is reflected by the peripheral portion of the perforated prism 66. The light reflected by the peripheral portion of the perforated prism 66 becomes a parallel light beam by a pupil lens 71, a relay lens 72, and a focusing lens 73, is incident on the opening portion of a six-hole aperture plate 74, and is split into six separate light beams. As shown in FIG. 2B, a wedge hexagonal prism 75 is composed of six prisms each having a slope on the outer side as seen from the direction of the optical axis OP. The six light beams generated by the six-hole aperture plate 74 are deflected by a predetermined angle by the wedge hexagonal prism 75. An imaging lens 76 projects each of the six light beams onto the image pickup device 77, thereby forming six point images centered around the optical axis OP as shown in FIG. 2C.

The focusing lens 73, the six-hole aperture plate 74, and the wedge hexagonal prism 75 are provided in a measurement unit 73A. The measurement unit 73A is configured to be movable in the direction along the optical axis. During the refractometry, the focusing lens 62 and the measurement unit 73A are moved in the direction of the optical axis in linkage with each other.

It should be noted that the refractometry light reception system 7 may include a conical prism in place of the wedge hexagonal prism 75. The conical prism is used to detect the light source image projected onto the fundus Ef as a ring pattern that has passed through the peripheral portion that is apart from the pupil center of or from the optical center of the eyeball of the subject's eye E by a predetermined distance.

(Interference Optical System 14)

The interference optical system 14 has the same configuration as the refractometry light projection system 6. The light beam emitted from the light source 141 passes through the same optical path and is projected onto the fundus Ef of the subject's eye E. In the case of performing the eyeball information measurement, the decentered prism 67 is retracted from the optical path, and the measurement light beam passes through the pupil center (or the optical center of the eyeball) of the subject's eye E and is projected onto the fundus Ef.

Further, the interference optical system 14 functions as a light reception system that detects returning light of the measurement light projected onto the fundus Ef in the OCT measurement. The light reception system includes the objective lens 51, the dichroic mirrors 52 and 49, the light beam decentered prism 67 with the rotation mechanism that can be inserted into and removed from the optical path, the perforated prism 66, the pupil lens 65, the reflection mirror 64, the relay lens 63, the focusing lens 62, the collimator lens 61, the fiber coupler 142, and a spectrometer 143.

The processor 9 controls each portion of the ophthalmic apparatus 1000. For example, the processor 9 controls the liquid crystal panel 41, the light source 141, the glare light source 81, the Z alignment light source 11, the XY alignment light source 21, a keratometry ring light source 32 of the keratometry plate 31, the focusing lenses 45, 62 and 73 (the measurement unit 73A on which the focusing lens 73 is mounted), the VCC lens 47, a retina and anterior chamber depth shutter 154, a corneal shutter 157, reference mirrors 156 and 159, the display unit 10, the light beam decentered prism 67 with the rotation mechanism that can be inserted into and removed from the optical path, and the like.

(Corneal Shape Measurement Function)

In the case of performing the keratometry, the processor 9 turns on the keratometry ring light source 32. The corneal shape measurement ring-shaped light beam (the keratometry plate 31) is projected onto the cornea C, and the light beam reflected by the cornea C is projected together with the anterior segment image E' on the image pickup device 58 by the observation system 5. The processor 9 applies predetermined calculation processing to the image acquired by the image pickup device 58 to calculate a parameter representing the shape of the cornea.

(Objective Measurement Function)

When performing refractometry, the processor 9 turns on the light source 141. The light emitted from the light source 141 passes through the fiber coupler 142 as described above, becomes a parallel light beam by the collimator lens 61, and is projected onto the fundus Ef by the refractometry light projection system 6. When the subject's eye E is a normal vision (emmetropia) (=0D), the end face of the fiber (the focal position of the collimator lens 61) and the position at which the fundus Ef of the subject's eye E is conjugate are the reference positions of the focusing lens 62. The light beam projected onto the fundus Ef in this state is reflected by the fundus Ef and passes through the refractometry light reception system 7. The opening portion of the six-hole aperture plate 74 and by the wedge hexagonal prism 75 disposed on the way generate the six separate light beams. The six separate light beams are projected onto the image pickup device 77. Since the subject's eye E is a normal vision, each of the six separate light beams are projected at a reference position (all at equal intervals from the center) on the image pickup device 77.

When the subject's eye is myopic, the projection position of each of the light beams is shifted in the direction toward the center on the image pickup device 77. When the subject's eye is hyperopic, the projection position of each of the light beams is shifted outward from the center. The processor 9 detects the shift amounts from the reference positions and calculates the refractive power of the subject's eye E. This is a known method. Alternatively, the processor 9 can move the focusing lens 62 and the measurement unit 73A (the focusing lens 73, the six-hole aperture plate 74, and the wedge hexagonal prism 75) and obtain the refractive power of the subject's eye E from the movement amount thereof.

(OCT Measurement Function)

Here, as an example of the OCT measurement, the case of determining the axial length (the distance between the vertex of the cornea and the retina) of the subject's eye E will be described. When performing the OCT measurement, the processor 9 turns on the light source 141. In synchronization with the lighting of the light source 141, the corneal shutter 157 is inserted in the optical path between a beam splitter 153 and a corneal reference mirror unit 161, and the retina and anterior chamber shutter 154 is retracted from the optical path between the beam splitter 153 and a retina and anterior chamber depth reference mirror unit 160. The light L0 emitted from the light source 141 is split into the measurement light LS and the reference light LR by the fiber coupler 142. The measurement light LS passes through the same optical path as the refractometry light projection system 6 and is projected onto the fundus Ef of the subject's eye E. At this time, the decentered prism 67 is retracted from the optical path. Further, the focusing lens 62 is moved based on the result of the refractive power measurement of the subject's eye E described above so that the fiber end face becomes conjugate with the fundus Ef of the subject's eye E. The light reflected by the fundus Ef returns through the same optical path, is projected onto the fiber end face, and reaches the fiber coupler 142.

On the other hand, the reference light LR is converted into a parallel light beam by the collimator lens 151 and is split into two light beams (one for the cornea and the other for the retina) by the beam splitter 153 with the ratio 50:50. The two light beams are converged on the reference mirrors (reflection mirrors) 156 and 159 by imaging lenses 155 and 158, respectively. Here, as described above, since the corneal shutter 157 is inserted in the optical path and the retina and anterior chamber shutter 154 is retracted from the optical path, only the light reflected from the reference mirror (retinal reference mirror) 156 returns through the same optical path and reaches the fiber coupler 142. The light reflected by the fundus Ef and the light reflected by the reference mirror 156 are superposed by the fiber coupler 142, and an interference signal (interference light LC) thus generated is guided to the spectrometer 143. In the spectrometer 143, the interference light LC is spatially separated into wavelength components and the wavelength components are projected onto a line sensor. The processor 9 applies known Fast Fourier Transform (FFT, hereinafter) to the signal output from the line sensor to extract information on the depth direction.

Figure 4A:
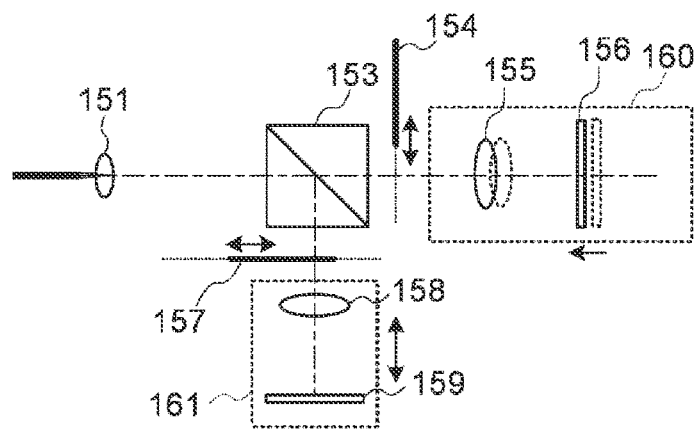
FIG. 4A is an explanatory diagram of the operation of the ophthalmic apparatus according to the embodiment.
Figure 4B:
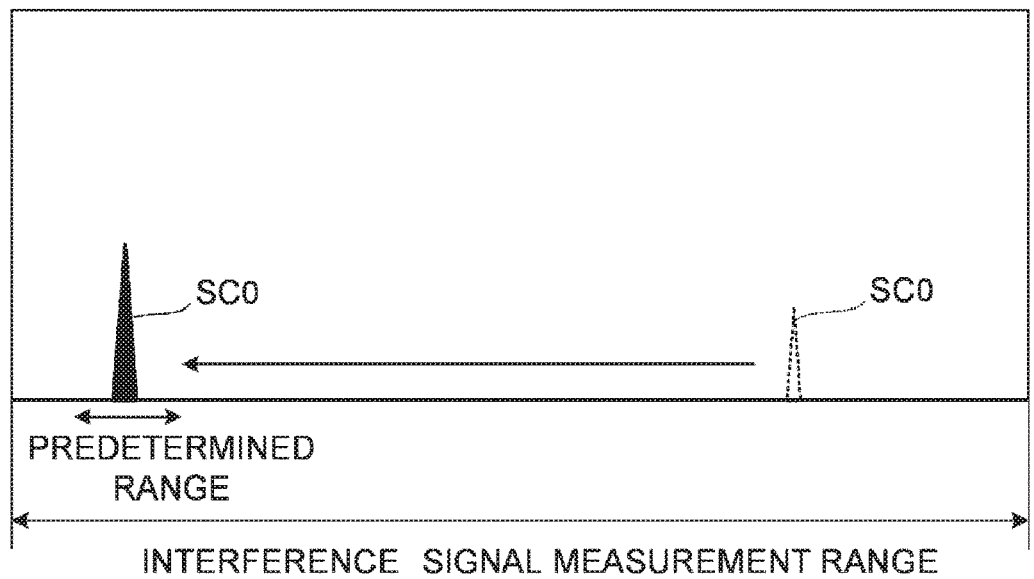
FIG. 4B is an explanatory diagram of the operation of the ophthalmic apparatus according to the embodiment.

The retina and anterior chamber depth reference mirror unit 160 and the corneal reference mirror unit 161 are moved so that the position of the interference signal is located at a predetermined position in the depth direction in accordance with the axial length of the subject's eye E. For example, the intensity change of the interference signal after FFT with respect to the depth direction is expressed as shown in FIG. 4B. By moving the retina and anterior chamber depth reference mirror unit 160 in the direction along the optical axis as shown in FIG. 4A, the position of the interference signal SC0 corresponding to the retina can be moved to a predetermined position within a predetermined range, as shown in FIG. 4B. Here, the position of the corneal reference mirror 159 may be fixed.

Figure 5A:
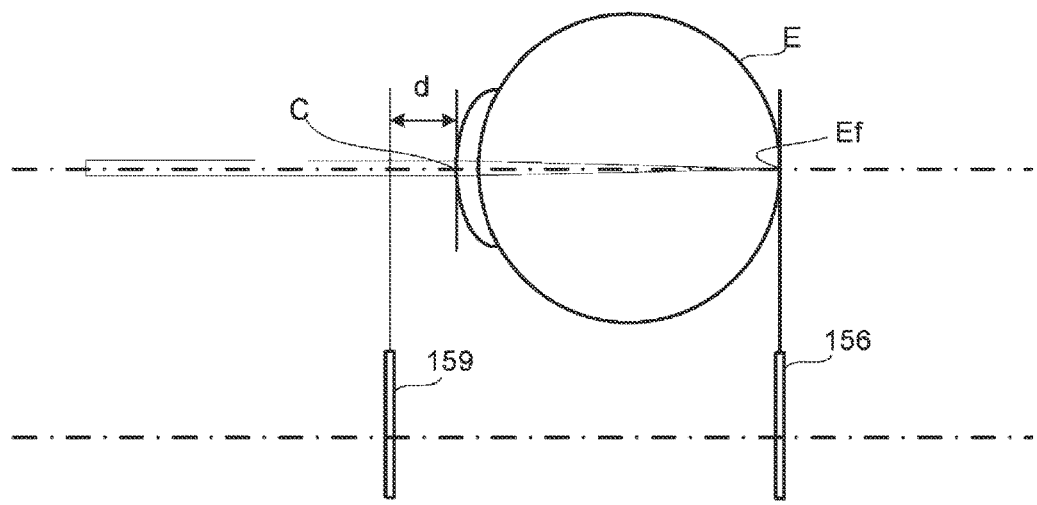
FIG. 5A is an explanatory diagram of the operation of the ophthalmic apparatus according to the embodiment.
Figure 5B:
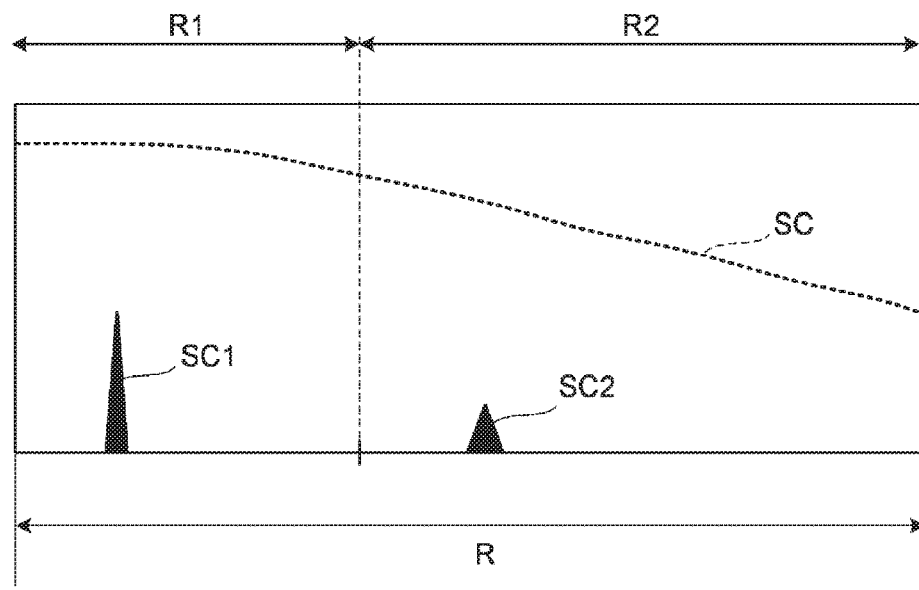
FIG. 5B is an explanatory diagram of the operation of the ophthalmic apparatus according to the embodiment.

Furthermore, since the coordinates of the vertex of the cornea are detected by the above-described Z alignment projection system 1, it is possible to always adjust the distance (working distance) between the vertex of the cornea and the objective lens 51 within a certain distance. Here, when the corneal shutter 157 is retracted from the optical path, an interference signal with the light reflected by the cornea C among the light projected onto the subject's eye E is simultaneously projected on the spectrometer 143. When the working distance is within a predetermined range, the corneal reference mirror 159 is disposed at a position separated from the corneal position by a distance d so as not to overlap with the interference signal SC1 corresponding to the retina (FIG. 5A). Therefore, as shown in FIG. 5B that represents the intensity change of the interference signal after FFT with respect to the depth direction same as in FIG. 4B, two interference signals (the interference signal SC1 corresponding to the retina and the interference signal SC2 corresponding to the cornea) can be acquired at the same time within the interference signal measurement range R. In particular, when the signal sensitivity S changes as shown in FIG. 5B, it is possible to acquire the two interference signals with high accuracy at the same time by detecting the interference signal SC1 corresponding to the retina with lower intensity in the measurement range R1 with higher signal sensitivity while detecting the interference signal SC2 corresponding to the cornea with higher intensity in the measurement range R2 with lower signal sensitivity.

When the interference optical system 14 has a configuration similar to that of general swept source type OCT apparatuses, the ophthalmic apparatus of the embodiment can include a wavelength tunable light source in place of the light source 141 that outputs low coherence light, and in this case the ophthalmic apparatus does not include an optical member that splits the interference light into spectral components. As for the configuration of the interference optical system 14, a known technology corresponding to the type of optical coherence tomography can be employed in an arbitrary manner.

The light source 141 outputs broadband low coherence light L0, such as a super luminescent diode (SLD). The light source 141 is, for example, a low coherence light source having a center wavelength in the range of 820 nm to 880 nm. With this, both the refractometry and the OCT measurement can be performed with the same light source while reducing the burden on the subject due to the visibility of the measurement light.

A glass block, a density filter, or the like may be arranged in the optical path of the reference light LR between the collimator lens 151 and the reference mirrors 156 and 159.

The glass block and the density filter serve as a delay member for matching the optical path length (optical distance) between the reference light LR and the measurement light LS. The glass block and the density filter also serve as a member for matching the dispersion characteristics between the reference light LR and the measurement light LS, and as a member for matching the dispersion characteristics between the corneal reference system (161) and the retina and anterior chamber depth reference system (160).

The spectrometer 143 includes, for example, a collimator lens, a diffraction grating, an imaging lens, and a CCD. The interference light LC incident on the spectrometer 143 is made into a parallel light beam by the collimator lens, and then is split into spectral components by the diffraction grating. The interference light LC having been split is projected on the imaging surface of the CCD by the imaging lens. The CCD detects the interference light LC, converts it into an electric detection signal, and outputs the detection signal to the processor 9. Based on the detection signal from the CCD, the processor 9 generates OCT information (for example, image data) of the cross section of the subject's eye E. Such processing includes, for example, noise removal (noise reduction), filtering, FFT, and the like similarly to the conventional spectral domain type optical coherence tomography.

In addition, when the interference optical system 14 has a configuration similar to general swept source type OCT apparatuses, the spectrometer 143 includes, for example, an optical splitter and a balanced photo diode (BPD). The interference light LC incident on the spectrometer 143 is split into a pair of interference light by the optical splitter. The BPD includes a pair of photodetectors that respectively detects the pair of interference light. The BPD outputs the difference between the pair of detection signals (the pair of detection results) acquired by the pair of photodetectors to the processor 9.

In the present embodiment, a Michelson interferometer is adopted, but any type of interferometer such as a Mach-Zehnder type can be adopted when appropriate.

(Subjective Measurement Function)

In the case of performing subjective measurement, the processor 9 drives the self-luminous liquid crystal panel 41 to display a desired target(s). Further, the processor 9 moves the focusing lens 45 to a position corresponding to the result of the objective measurement. Similarly, based on the state of astigmatism (astigmatic power, astigmatic axis angle) of the subject's eye E obtained by the objective measurement, the processor 9 can control the VCC lens 47 so that the astigmatic state is corrected. The astigmatic power can be changed by independently rotating two cylinder lenses constituting the VCC lens 47 in mutually opposite directions. The astigmatic axis angle can be changed by rotating the two cylinder lenses constituting the VCC lens 47 by the same angle in the same direction.

When a visual target(s) is selected by the examiner or by the processor 9, the processor 9 drives the liquid crystal panel 41 to display the selected visual target(s). Light from the visual target(s) travels through the relay lens 42, the reflection mirror 43, the half mirror 44, the focusing lens 45, the relay lens 46, the VCC lens 47, the reflection mirror 48, the dichroic mirrors 49 and 52, and the objective lens 51, and is projected onto the fundus Ef.

The subject responds to the visual target(s) projected on the fundus Ef. For example, in the case where a visual acuity measurement chart is used, the visual acuity value of the subject's eye is determined based on the responses from the subject. For example, in the case of the astigmatism test, a dot chart is displayed, and the astigmatic power of the subject's eye is determined based on the responses from the subject. Selection of the visual target and response of the subject with respect to the selected visual target are repeatedly performed on the basis of the determination of the examiner or of the processor 9. The examiner or the processor 9 determines the visual acuity values or the prescription values (S, C, A) based on the responses from the subject.

Further, when the glare test is performed, the processor 9 turns on the glare light source 81 and the subjective measurement is performed in this state. Further, when the contrast test is performed, the processor 9 drives the liquid crystal panel 41 to change the contrast of the visual target(s) displayed.

In the present embodiment, the followings are known: the configuration of the fixation and subjective measurement system 4; the configurations of the Z alignment projection system 1 and the configuration of the XY alignment spot projection system 2; the configuration of the keratometry system; the principle of the measurement of the refractive power (the principle of the refractometry); the principle of the subjective measurement; the principle of the measurement of the shape of the cornea. Thus, their detailed description will be omitted.

(Configuration of Information Processing System)

Figure 6:
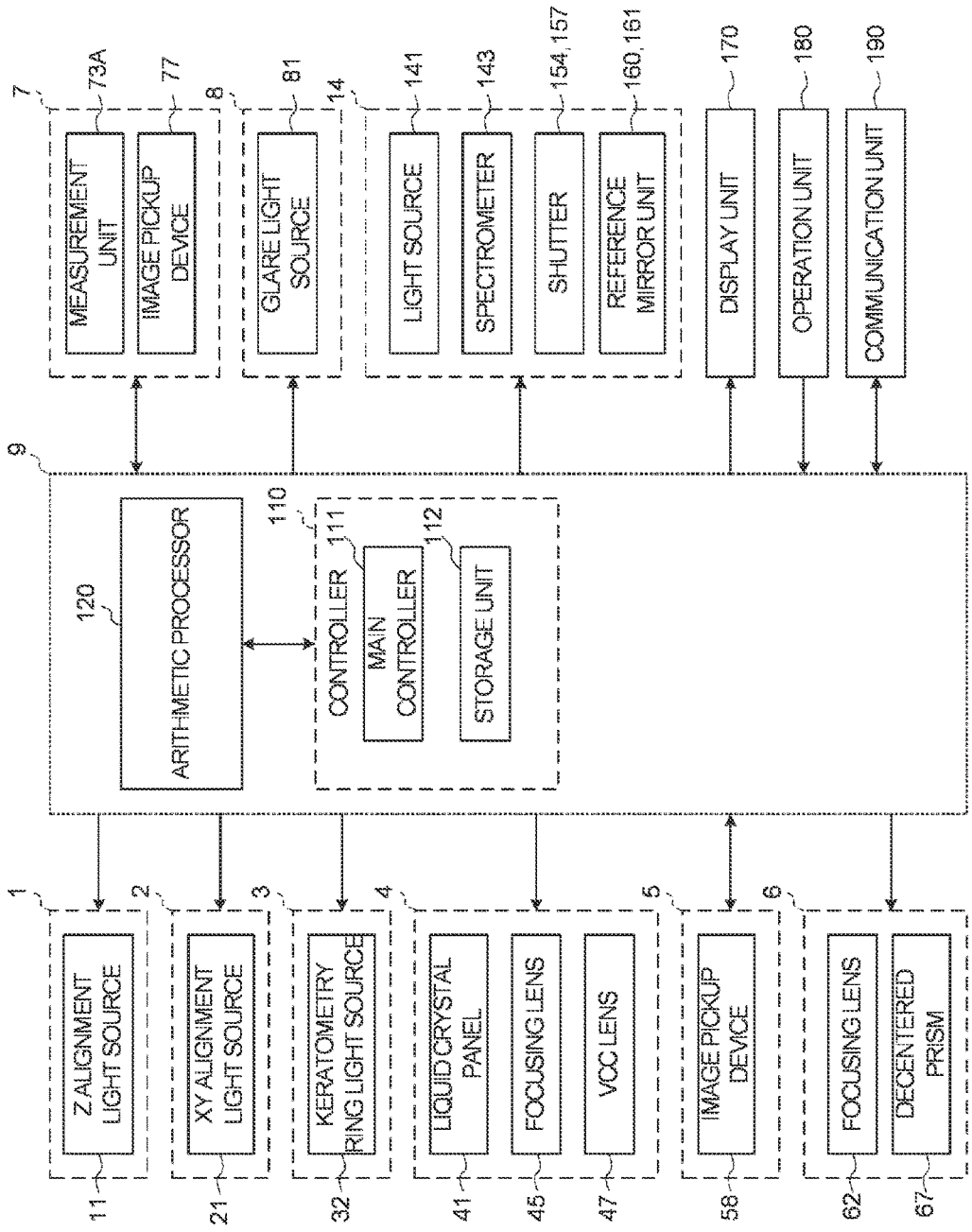
FIG. 6 is a schematic diagram illustrating an example of the configuration of the ophthalmic apparatus according to the embodiment.
Figure 7:
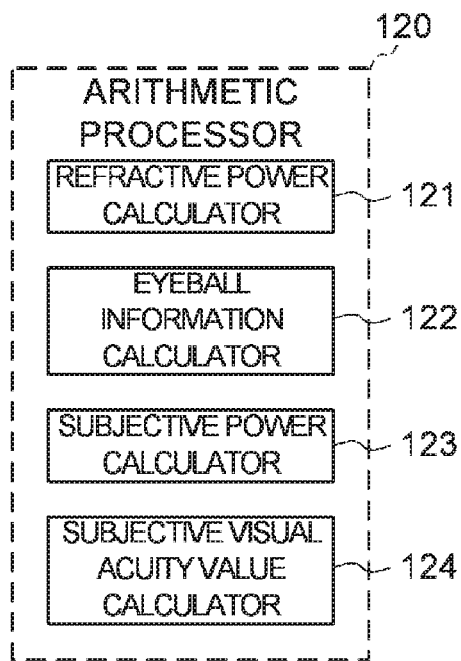
FIG. 7 is a schematic diagram illustrating an example of the configuration of the ophthalmic apparatus according to the embodiment.

The information processing system of the ophthalmic apparatus 1000 will be described. FIG. 6 and FIG. 7 shows an example of the functional configuration of the information processing system of the ophthalmic apparatus 1000. The information processing system includes a controller 110, an arithmetic processor 120, a display unit 170, an operation unit 180, and a communication unit 190. The controller 110 controls the arithmetic processor 120, the Z alignment projection system 1 (the Z alignment light source 11), the XY alignment spot projection system 2 (the XY alignment light source 21), a keratometry ring projection system 3 (the keratometry ring light source 32), the fixation and subjective measurement system 4, the observation system 5, the refractometry light projection system 6 (the decentered prism 67), the refractometry light reception system 7, the glare light projection system 8 (the glare light source 81), the interference optical system 14, the display unit 170, and the communication unit 190. The processor 9 includes, for example, the controller 110 and the arithmetic processor 120.

(Controller 110)

The controller 110 includes a main controller 111 and a storage unit 112. The controller 110 includes, for example, a microprocessor, a Random Access Memory (RAM), a Read Only Memory (ROM), a hard disk drive, and the like.

(Main Controller 111)

The main controller 111 performs various controls of the ophthalmic apparatus 1000. In particular, the main controller 111 controls the Z alignment light source 11, the XY alignment light source 21, the keratometry ring light source 32, the liquid crystal panel 41, the focusing lens 45, and the VCC lens 47. Further, the main controller 111 controls the focusing lens 62, the decentered prism 67, the measurement unit 73A, the glare light source 81, the light source 141, the retina and anterior chamber shutter 154, the corneal shutter 157, the retina and anterior chamber depth reference mirror unit 160, the corneal reference mirror unit 161, and the like. In particular, the main controller 111 controls the rotation, insertion and removal of the decentered prism 67. Further, the main controller 111 moves the measurement unit 73A and the focusing lens 62 in linkage with each other in the directions along the optical axes. As a result, the focal position of the refractometry light reception system 7 is changed. In addition, the main controller 111 controls the image pickup devices 58 and 57 and the spectrometer 143 to take in the signals acquired by them, and controls the arithmetic processor 120 to execute image formation or the like.

Further, the main controller 111 performs a process of writing data in the storage unit 112 and a process of retrieving data from the storage unit 112.
(Storage Unit 112)

The storage unit 112 stores various kinds of data. Examples of the data stored in the storage unit 112 include setting information of an optical element(s) in each operation mode, image data of OCT information, image data of fundus images, subject's eye information, and the like. The subject's eye information includes information on the subject such as patient ID and name, and information on the subject's eye such as identification information of the left eye/right eye. In addition, the storage unit 112 stores various kinds of computer programs and data for operating the ophthalmic apparatus 1000.
(Display Unit 170, Operation Unit 180)

Upon receiving control of the controller 110, the display unit 170 displays information. The display unit 170 includes the display unit 10 shown in FIG. 1 and the like.

The operation unit 180 is used for operating the ophthalmic apparatus 1000. The operation unit 180 includes various kinds of hardware keys (the joystick 800, buttons, switches, etc.) provided in the ophthalmic apparatus 1000. Further, the operation unit 180 includes various kinds of software keys (buttons, icons, menus, etc.) displayed on the touch panel type display screen 10a.

At least part of the display unit 170 and of the operation unit 180 may be integrally configured. A touch panel type display screen 10a is a typical example thereof.
(Communication Unit 190)

The communication unit 190 has a function of communicating with the external device 900 shown in FIG. 1. The communication unit 190 may be provided in the processor 9, for example. The communication unit 190 has a configuration according to the mode of communication with the external device 900.
(Arithmetic Processor 120)

As shown in FIG. 7, the arithmetic processor 120 includes a refractive power calculator 121, an eyeball information calculator 122, a subjective power calculator 123, and a subjective visual acuity value calculator 124.

The refractive power calculator 121 calculate refractive power of an ocular optical system of the subject's eye E based on the result of the detection of the returning light of the light emitted from the light source 141 and projected on the fundus Ef of the subject's eye E. For example, the refractive power calculator 121 calculates the eye refractive power by applying predetermined calculation processing to the images of the six light beams acquired by the image pickup device 77 in the refractometry light reception system 7. In a specific example thereof, as described above, the refractive power calculator 121 may be configured to calculate the amounts of the shifts of the positions of the images of the six light beams projected on the image pickup device 77 from the respective reference positions, and to determine the eye refractive power from the amounts of the shifts calculated. When the conical prism is employed, the refractive power calculator 121 may be configured to determine the deformation and/or the displacement of the image of the ring pattern acquired by the image pickup device 77 from the reference pattern, and to determine the eye refractive power based on the deformation and/or the displacement determined.

The eyeball information calculator 122 acquire eyeball information representing the structure of the subject's eye E based on the result of the detection of the returning light of the light emitted from the light source 141 and projected on the subject's eye E. The eyeball information includes at least one of the axial length, the corneal thickness, the anterior chamber depth, and the crystalline lens thickness.

The eyeball information calculator 122, for example, may be configured to apply arithmetic processing to the keratometry ring image acquired by the image pickup device 58 in the observation system 5 to calculate the corneal curvature radius of the steepest meridian (i.e., first principal meridian) and/or the flattest meridian (i.e., second principal meridian) of the anterior surface of the cornea. In addition, the eyeball information calculator 122 may be configured to calculate, based on the corneal curvature radius calculated, the corneal refractive power, the corneal astigmatic power, the corneal astigmatic axis angle, and the like.

In addition, the controller 110 can control the interference optical system 14 and the eyeball information calculator 122 to acquire the eyeball information such as the axial length based on the signals input according to the responses from the subject in the visual acuity measurement. Examples of the signals input according to the responses from the subject include the following signals: a signal for the controller 110 to start the eyeball information measurement (e.g., axial length measurement) based on the responses input by the subject in the visual acuity measurement; a signal generated when the visual acuity value at the time of providing a response is equal to or more than a predetermined threshold value; and a signal generated based on the instruction from the examiner or from the subject in the visual acuity measurement to start the eyeball information measurement (e.g., axial length measurement).

Further, in the case of starting the eyeball information measurement, the controller 110 may be configured to control the interference optical system 14 and the eyeball information calculator 122 to perform acquisition of eyeball information when the visual acuity value corresponding to the visual target being projected at the time of response from the subject is equal to or more than the threshold value. The threshold value may be a predetermined value, or may be a value determined based on the visual acuity measurement value of the subject's eye acquired in the past.

The interference optical system 14 and the eyeball information calculator 122 are an example of an "eyeball information measurement unit" according to the present embodiment. The observation system 5, the keratometry plate 31, the Z alignment projection system 1, the XY alignment spot projection system 2, and the eyeball information calculator 122 are an example of a "corneal shape measurement unit" according to the present embodiment.

The subjective power calculator 123 calculates the power of the IOL using a known calculation formula based on the refractive power of the ocular optical system of the subject's eye E and the eyeball information representing the structure of the subject's eye E. For example, the subjective power calculator 123 determines the power of the IOL using a known calculation formula based on the axial length, the corneal thickness, the anterior chamber depth and the crystalline lens thickness.

The subjective visual acuity value calculator 124 obtains the visual acuity value of the subject's eye based on the subject's replies to the visual targets projected on the fundus Ef of the subject.

(Example of Operation)

An example of the operation of the ophthalmic apparatus 1000 according to the present embodiment will be described.

Figure 8:
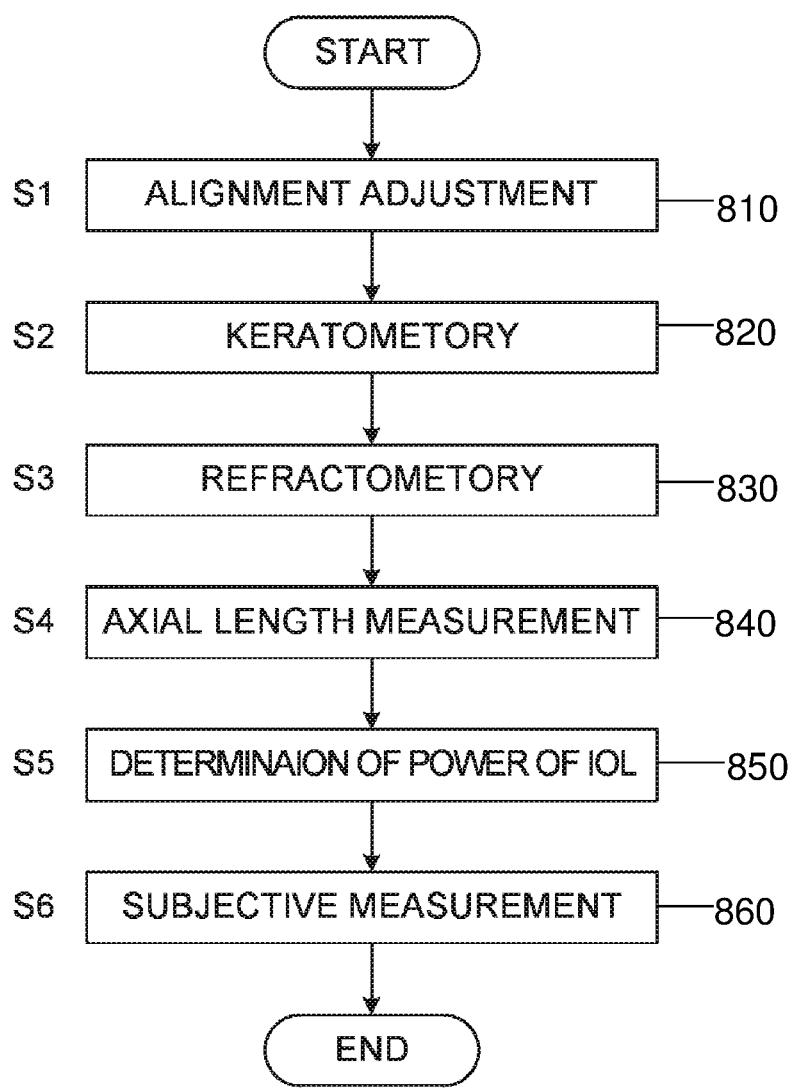
FIG. 8 is a flowchart illustrating an example of the operation of the ophthalmic apparatus according to the embodiment.

FIG. 8 shows a flowchart of an example of the operation of the ophthalmic apparatus 1000 according to the first embodiment.

To start with, at step 810 (S1), the face of the subject with the face support 500 is fixed, and then the head unit 400 is moved to the test position of the subject's eye E. The test position is a position where the test of the subject's eye E can be performed. The subject's eye E is placed at the test position through the alignment described above (that is, by the use of the Z alignment projection system 1, the XY alignment spot projection system 2, and the observation system 5). The controller 110 performs the movement of the head unit 400 according to an operation or instruction by a user or according to an instruction by the controller 110. That is, the movement of the head unit 400 to the test position of the subject's eye E and the preparation for the objective measurement are carried out.

For example, the controller 110 can turn off the Z alignment light source 11 and the XY alignment light source 21, and then prepare for the keratometry in the next step and the like.

When the alignment state in S1 becomes appropriate, the ophthalmic apparatus 1000 shifts in step 820 (S2), to a keratometry mode. The transition to the keratometry mode is performed in response to an instruction from the controller 110 or according to an operation or instruction to the operation unit 180 by the user.

Upon having shifted to the keratometry mode, the controller 110 turns on the keratometry ring light source 32. When the light is emitted from the keratometry ring light source 32, a ring-shaped light beam for corneal shape measurement is projected onto the cornea C. The eyeball information calculator 122 applies arithmetic processing to the image acquired by the image pickup device 58 to calculate the corneal curvature radius. Furthermore, based on the corneal curvature radius calculated, the eyeball information calculator 122 calculates the corneal refractive power, the corneal astigmatic power, and the corneal astigmatic axis angle. The calculated corneal refractive power and the like are stored in the storage unit 112 in the controller 110.

Next, the ophthalmic apparatus 1000 shifts, at step 830 (S3), to a refractometry mode. The shift to the refractometry mode is performed according to an instruction from the controller 110 or according to an operation or instruction to the operation unit 180 by the user. In S3, refractometry is performed as described above, and the refractive power calculator 121 calculates the eye refractive power. The calculated refractive power and the like are stored in the storage unit 112 in the controller 110.

Next, at step 840 (S4), the ophthalmic apparatus 1000 shifts to an OCT measurement mode. The shift to the OCT measurement mode is performed according to an instruction from the controller 110 or according to an operation or instruction to the operation unit 180 by the user. In S4, OCT measurement is performed as described above, and the eyeball information calculator 122 calculates eyeball information such as the axial length. In the controller 110, the calculated eyeball information is stored in the storage unit 112.

Next, at step 850 (S5), the subjective power calculator 123 determines the power of the IOL based on the refractive power of the ocular optical system of the subject's eye E and the eyeball information representing the structure of the subject's eye E acquired in S2 to S4.

Next, at step 860 (S6) the ophthalmic apparatus 1000 shifts to a subjective measurement mode. The shift to the subjective measurement mode is performed according to an instruction from the controller 110 or according to an operation or instruction to the operation unit 180 by the user. In S6, the subjective measurement is performed as described above, and the subjective visual acuity value calculator 124 determines the visual acuity value. In the controller 110, the determined visual acuity value is stored in the storage unit 112.

It should be noted that the subjective measurement in S6 may be performed simultaneously with the measurement of the axial length in S4. In such a case, in the subject's eye, the optical axis of the optical system for performing the subjective measurement (i.e., the optical axis of the fixation and subjective measurement system 4) and the optical axis of the optical system for measuring the axial length (i.e., the optical axis of the interference optical system) substantially coincide, as shown in FIG. 2. In other words, the measurement of the axial length is performed in a state in which the visual axis (axis opticus) substantially coincides with these optical axes. Conventionally, it has been impossible to measure an axial length in a state where the positional relationship between the measurement optical axis and the visual axis is constant. However, according to the present embodiment, the axial length measurement can be performed in a state in which the positional relationship between the measurement optical axis and the visual axis is constant. Therefore, it becomes possible to measure the axial length in a state in which the positional relationship between the subject's eye and the measurement optical system is appropriate. As a result, the accuracy of measuring the axial length is improved, and the power of the IOL can be determined with high accuracy.

In S6, the contrast test and/or the glare test may be performed. For example, it is assumed that the user has input an instruction for performing the contrast test on the subject's eye to the operation unit 180 after the completion of the subjective measurement of the subject's eye. Upon receiving the instruction, the controller 110 prepares for performing the contrast test. Then, the contrast test of the subject's eye is carried out. In the contrast test, the contrast of a visual target(s), the thickness and density of the lines of a stripe visual chart(s) are changed. The test determines to what extent the subject's eye is capable of distinguishing the visual target(s). The controller 110 stores the acquired contrast visual acuity value in the storage unit 112. As a result, the contrast visual acuity value after the application of the IOL is acquired. In addition, the subject and the examiner can determine whether or not the application of the IOL is possible.

When the user inputs an instruction for performing the glare test on the subject's eye to the operation unit 180 after the contrast test has been completed, the controller 110 receives the instruction and then prepares for performing the glare test. The preparation includes lighting of the glare light source 81 and the like. Then, the glare test of the subject's eye is carried out. The glare test determines to what extent the subject's eye is capable of distinguishing the visual target(s) in a state where the light from the glare light source 81 is applied to the visual target(s). The controller 110 stores the acquired glare visual acuity value in the storage unit 112. As a result, the glare visual acuity value after the application of the IOL is acquired. In addition, the subject and the examiner can determine whether or not the application of the IOL is possible.

Thus, the example of the operation of the ophthalmic apparatus 1000 is terminated (END).

(Actions and Effects)

The actions and effects of the ophthalmic apparatus 1000 according to the embodiment will be described.

The ophthalmic apparatus includes a refractive power measurement unit (for example, the system of projecting the measurement light of the interference optical system 14, the refractometry light reception system 7, and the refractive power calculator 121) and an eyeball information measurement unit (for example, the interference optical system 14 and the eyeball information calculator 122). The refractive power measurement unit is configured to project light from a light source (for example, the light source 141) onto the subject's eye E and detect returning light thereof to determine the refractive power of the ocular optical system of the subject's eye E. The eyeball information measurement unit is configured to project light from the light source (for example, the light source 141) onto the subject's eye E and detect returning light thereof to determine the eyeball information representing the structure of the subject's eye E.

According to such a configuration, the light source for acquiring the refractive power and the light source for acquiring the eyeball information can be a common light source. Thus, it is possible to reduce the size of the ophthalmic apparatus capable of performing a plurality of kinds of measurements performed in order to determine the power of an IOL before cataract surgery.

In addition, part of the optical path of the light from the light source formed by the refractive power measurement unit and part of the optical path of the light from the light source formed by the eyeball information measurement unit may be common.

According to such a configuration, the light source for acquiring the refractive power and the light source for acquiring the eyeball information can be in common, and also the parts of the optical paths thereof can be in common. Thus, it is possible to reduce the size of the ophthalmic apparatus capable of performing a plurality of kinds of measurements performed in order to determine the power of an IOL before cataract surgery.

In addition, the refractive power measurement unit includes the followings: a projection system configured to project the light from the light source onto the fundus of the subject's eye through the pupil center of or through the optical center of the eyeball of the subject's eye (for example, the system of projecting measurement light of the interference optical system 14); a light reception system configured to receive light that has passed through a peripheral portion that is apart from the pupil center of or from the optical center of the eyeball of the subject's eye by a predetermined distance, among the light reflected from the fundus (for example, the refractometry light reception system 7); and a decentered member provided at a position substantially conjugate with the pupil of the subject's eye in a common optical path of the projection system and the light reception system (for example, the decentered prism 67).

According to such a configuration, as described above, in the ophthalmic apparatus capable of performing a plurality of kinds of measurements performed in order to determine the power of an IOL before cataract surgery, it is possible to equalize the unevenness of the received light beams due to a disease or the like present on the surface of the fundus on which the measurement light for acquiring the refractive power is projected. This improves the accuracy of the measurements.

Further, the light reception system may include a wedge prism configured to detect the light source image projected on the fundus as a plurality of point images that has passed through the aforementioned peripheral portion (for example, the wedge hexagonal prism 75).

According to such a configuration, the measurement light of the refractometry can be projected through the pupil center of the subject's eye E. Thus, scattering of the measurement light due to opacity of the crystalline lens and the like can be suppressed and the accuracy of the measurements of the refractive power can be improved as compared with the case where a ring-shaped light beam is projected from the peripheral portion of the pupil onto the fundus as the measurement light.

In addition, the light reception system may include a conical prism configured to detect a light source image projected on the fundus as a ring pattern that has passed through the aforementioned peripheral portion.

According to such a configuration as well, the measurement light can be projected from the pupil center of the subject's eye E in the refractometry. Thus, scattering of the measurement light due to opacity of the crystalline lens and the like can be suppressed and the accuracy of the measurements of the refractive power can be improved as compared with the case where a ring-shaped light beam is projected from the peripheral portion of the pupil onto the fundus as the measurement light.

Further, the eyeball information measurement unit may include an interference optical system (for example, the interference optical system 14) and an eyeball information calculator (for example, the eyeball information calculator 122). The interference optical system is configured to split the light from the light source into reference light and measurement light, to project the measurement light onto the subject's eye, and to detect the interference light generated from returning light of the measurement light and the reference light. The eyeball information calculator is configured to calculate the eyeball information based on the result of the detection of the interference light acquired by the interference optical system.

According to such a configuration, the eyeball information can be obtained by a method of OCT using the light source for acquiring the refractive power.

In addition, the eyeball information measurement unit may include a splitting member configured to generate a plurality of reference light from the light from the light source (for example, the fiber coupler 142 and the beam splitter 153) and may acquire the eyeball information from the result of the detection of the interference light generated from reflected light of the measurement light from a plurality of positions of the subject's eye and the plurality of reference light.

According to such a configuration, the eyeball information on the plurality of positions of the subject's eye can be easily acquired.

Also, the eyeball information may include at least one of an axial length, a corneal thickness, an anterior chamber depth, and a crystalline lens thickness.

According to such a configuration, it is possible to reduce the size of the ophthalmic apparatus capable of measuring parameters necessary for a known calculation formula (for example, SRK formula) to determine the power of an IOL.

Further, the ophthalmic apparatus may include a power calculator (for example, the subjective power calculator 123) configured to calculate the power of an IOL based on the refractive power determined by the refractive power measurement unit and on the eyeball information determined by the eyeball information measurement unit.

According to such a configuration, it is possible to reduce the size of the ophthalmic apparatus capable of performing a plurality of kinds of measurements before cataract surgery and of determining the power of the IOL based on the results of these measurements.

In addition, the ophthalmic apparatus may include a corneal shape measurement unit configured to project predetermined pattern light onto a cornea of the subject's eye, and based on the result of the detection of returning light of the pattern light, to determine a parameter representing a shape of the cornea (for example, the observation system 5, the keratometry plate 31, Z alignment projection system 1, the XY alignment spot projection system 2, and the eyeball information calculator 122).

According to such a configuration, it is possible to reduce the size of the ophthalmic apparatus capable of performing keratometry as the plurality of kinds of measurements performed before cataract surgery.

Further, the ophthalmic apparatus may include a visual target projection unit configured to project a visual target(s) for a visual acuity measurement onto the fundus of the subject's eye (for example, the fixation and subjective measurement system 4).

According to such a configuration, it is possible to reduce the size of the ophthalmic apparatus capable of performing subjective measurement as the plurality of kinds of measurements performed before cataract surgery.

Further, the light source may be a low coherence light source whose center wavelength is in the range of 820 nm to 880 nm.

According to such a configuration, it is possible to provide an ophthalmic apparatus capable of acquiring aberration information and of acquiring eyeball information with the same light source while reducing the burden on the subject due to visibility of the measurement light.

Also, the ophthalmic apparatus may include: the visual target projection unit configured to project a visual target(s) for a visual acuity measurement onto the fundus of the subject's eye (for example, the fixation and subjective measurement system 4); and the eyeball information measurement unit configured to project light from the light source (for example, the light source 141) onto the subject's eye and detect returning light thereof to acquire eyeball information representing the structure of the subject's eye (for example, the interference optical system 14 and the eyeball information calculator 122).

According to such a configuration, it is possible to reduce the size of the ophthalmic apparatus capable of subjective measurement and of acquisition of eyeball information. Since the subjective measurement and the acquisition of the eyeball information can be performed with a single ophthalmic apparatus, for example, it possible to acquire the eyeball information of the subject's eye in a state in which the positional relationship is maintained between the subject's eye undergoing the subjective measurement and the measurement optical system thereof.

Further, the ophthalmic apparatus may include an optical path combining member configured to combine an optical path for projecting the visual target(s) and an optical path for acquiring the eyeball information (for example, the dichroic mirrors 49, 52). In addition, the ophthalmic apparatus may be configured to guide the light for projecting the visual target(s) and the light for acquiring the eyeball information to the subject's eye through the combined optical path formed by the optical path combining member.

According to such a configuration, the optical axis of the optical system for the subjective measurement and the optical axis of the optical system for acquiring the eyeball information are coaxial with each other in the subject's eye. Therefore, the eyeball information measurement is performed in a state where the visual axis is substantially matched with these optical axes. This makes it possible to acquire the eyeball information in a state in which the positional relationship between the subject's eye E and the measurement optical system thereof is appropriate. Thus, the accuracy of the measurement of the eyeball information is improved, and the power of the IOL can be determined with high accuracy.

In addition, the eyeball information measurement unit may acquire the eyeball information of the subject's eye when the visual acuity measurement using the visual target(s) projected by the visual target projection unit is being performed. Alternatively, the eyeball information measurement unit may acquire the eyeball information of the subject's eye immediately after the visual acuity measurement.

According to such a configuration, it is possible to acquire the eyeball information in a state in which the positional relationship between the subject's eye undergoing the subjective measurement and the measurement optical system thereof is maintained.

Also, the ophthalmic apparatus may include a controller configured to control the eyeball information measurement unit to acquire eyeball information based on a signal input according to a response from the subject in the visual acuity measurement.

With such a configuration, according to the state of the subjective measurement, the acquisition of the eyeball information can be performed in a state in which the positional relationship between the subject's eye and the measurement optical system thereof is maintained.

Further, the controller may control the eyeball information measurement unit to acquire the eyeball information when the visual acuity value corresponding to the visual target projected at the time of a response from the subject is equal to or more than the threshold value.

With such a configuration, according to the state of the subjective measurement, it is possible to acquire the eyeball information in a state in which the positional relationship between the subject's eye and the measurement optical system thereof is maintained.

Further, the ophthalmic apparatus may include a glare light projection system (for example, the glare light projection system 8) configured to project glare light onto the subject's eye in parallel to the projection of the visual target(s) by the visual target projection unit.

According to such a configuration, furthermore, it is possible to reduce the size of the ophthalmic apparatus also capable of performing the glare test.

In addition, the visual target projection unit may be capable of changing the contrast of the visual target(s) projected on the subject's eye.

According to such a configuration, furthermore, it is possible to reduce the size of the ophthalmic apparatus also capable of performing the contrast test.

In the first embodiment, the case has been described in which measurements are performed based on the image of returning light of the measurement light acquired by the refractometry light reception system 7 in the refractometry. However, the configurations of the ophthalmic apparatuses according to embodiments are not limited to this. In the second embodiment, measurements are performed using a Hartmann plate and an area sensor in the refractometry. Hereinafter, an ophthalmic apparatus according to the second embodiment will be described focusing on differences from the first embodiment.

Figure 9:
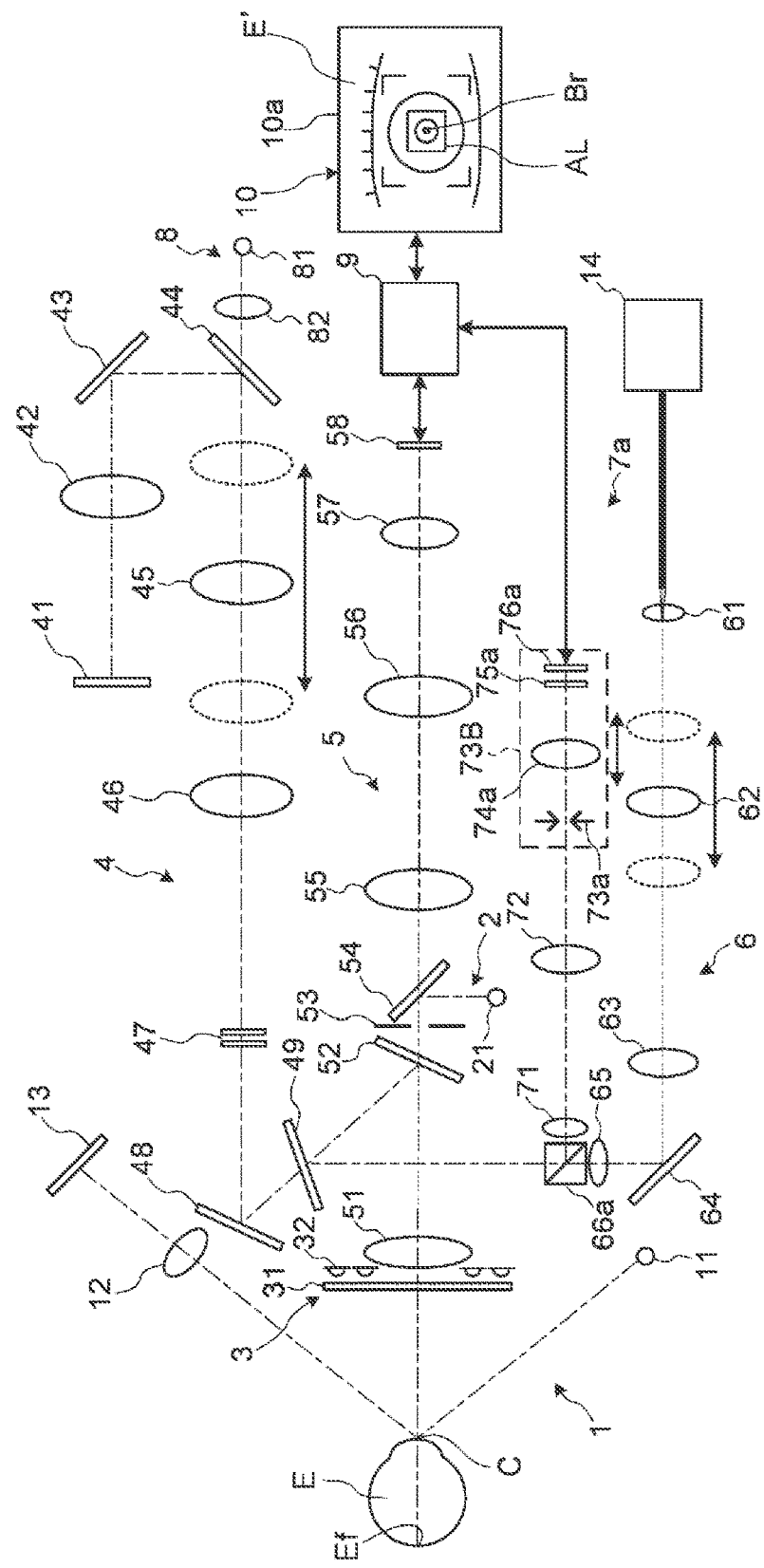
FIG. 9 is a schematic diagram illustrating an example of the configuration of the ophthalmic apparatus according to the embodiment.

FIG. 9 shows an example of the configuration of the ophthalmic apparatus according to the second embodiment. In FIG. 9, parts similar to those in FIG. 2 are denoted by the same reference numerals, and description thereof is omitted as appropriate.

The configuration of an ophthalmic apparatus 1000a according to the second embodiment is different from that of the ophthalmic apparatus 1000 according to the first embodiment shown in FIG. 2 in that a wavefront measurement optical system 7a is provided instead of the refractometry light reception system 7. The wavefront measurement optical system 7a includes an area sensor 76a, a Hartmann plate 75a, an imaging lens 74a, a diaphragm 73a, the relay lens 72, the pupil lens 71, a beam splitter 66a, the dichroic mirrors 49 and 52, and the objective lens 51. The diaphragm 73a, the imaging lens 74a, the Hartmann plate 75a, and the area sensor 76a are provided in a measurement unit 73B. The measurement unit 73B is configured to be movable in the direction along the optical axis. When measuring refractive power, the focusing lens 62 and the measurement unit 73B are moved in the directions along the optical axes in linkage with each other.

The Hartmann plate 75a is provided in the optical path of returning light from the subject's eye E. The Hartmann plate 75a is an optical element that splits the light beam incident from the imaging lens 74a into a plurality of light beams. The Hartmann plate 75a is a diaphragm in which a plurality of pinholes are formed in a predetermined arrangement on a light-shielding plate. When a parallel light beam of measurement light is incident on the Hartmann plate 75a, the images of a plurality of returning light beams corresponding to the arrangement of the plurality of pinholes are formed on the area sensor 76a. A plurality of image pickup elements is arranged on the face of the area sensor 76a. The results of the detections of the images of the returning light beams acquired by the image pickup elements are sent to the processor 9.

The returning light from the subject's eye E is converged by the objective lens 51, travels through the dichroic mirrors 52 and 49, and part of the returning light is reflected by the beam splitter 66a. The returning light reflected by the beam splitter 66a travels through the pupil lens 71, the relay lens 72, the diaphragm 73, and the imaging lens 74a, and is split into a plurality of light beams by the Hartmann plate 75a. The area sensor 76a detects the images of the returning light on a predetermined area basis.

Figure 10:
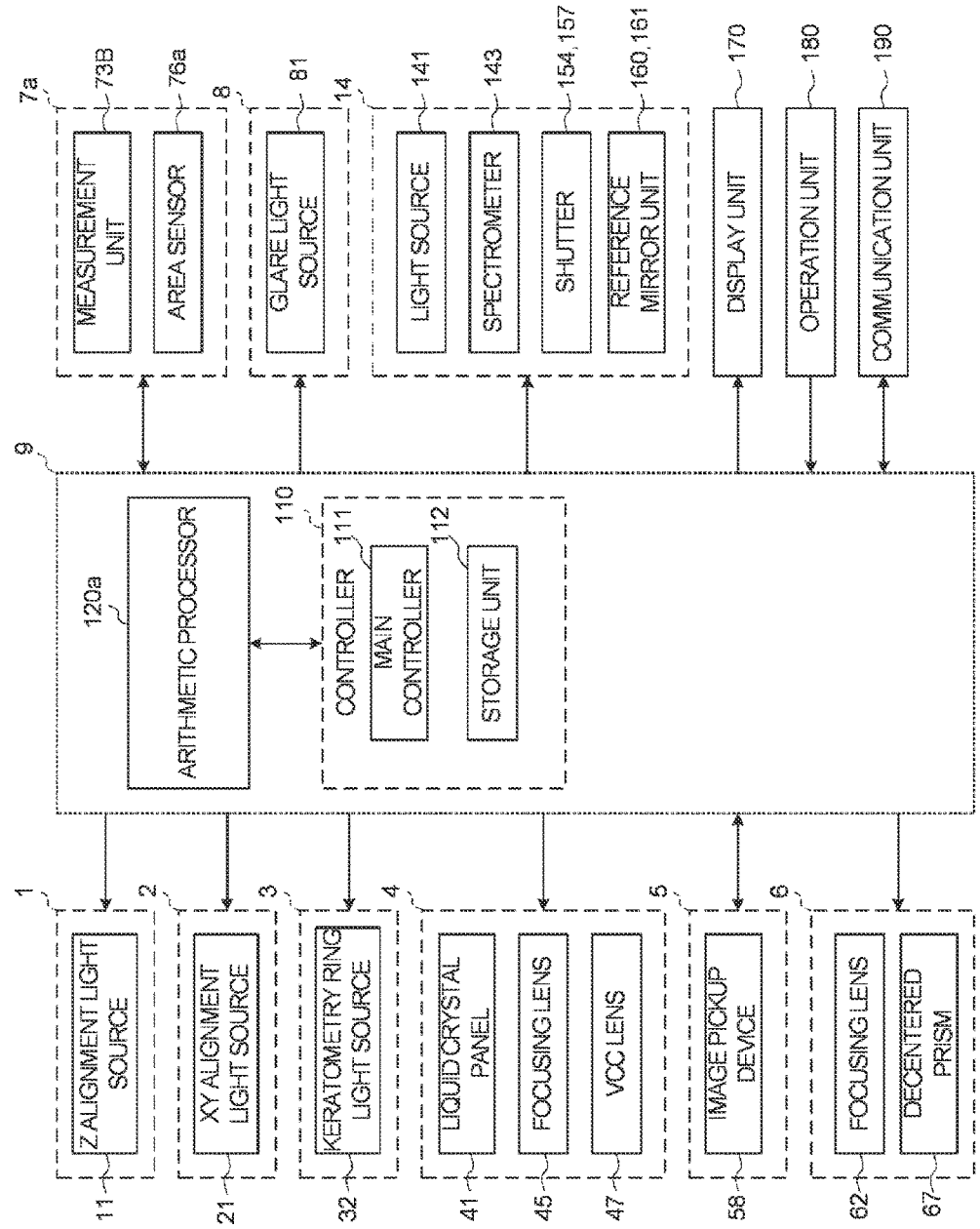
FIG. 10 is a schematic diagram illustrating an example of the configuration of the ophthalmic apparatus according to the embodiment.
Figure 11:
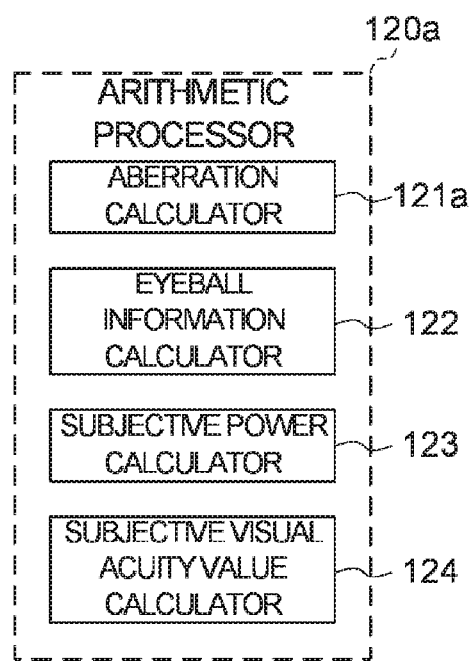
FIG. 11 is a schematic diagram illustrating an example of the configuration of the ophthalmic apparatus according to the embodiment.

FIG. 10 and FIG. 11 show an example of a functional configuration of the information processing system according to the second embodiment. In FIG. 10, parts similar to those in FIG. 6 are denoted by the same reference numerals, and description thereof is omitted as appropriate. In FIG. 11, parts similar to those in FIG. 7 are denoted by the same reference numerals, and description thereof is omitted as appropriate.

In this embodiment, an arithmetic processor 120a is provided in place of the arithmetic processor 120 in FIG. 6. The arithmetic processor 120a (the processor 9) acquires the result of the detection of the images of the returning light by the area sensor 76a. Further, the main controller 111 controls the measurement unit 73B and the focusing lens 62 to move in the directions along the optical axes in linkage with each other. As a result, the focal position of the wavefront measurement optical system 7a changes. In addition, the main controller 111 controls the image pickup device 58, the area sensor 76a, and the spectrometer 143 to take in signals acquired by them, and controls the arithmetic processor 120a to form an image or the like.

The arithmetic processor 120a includes an aberration calculator 121a, the eyeball information calculator 122, the subjective power calculator 123, and the subjective visual acuity value calculator 124.

The aberration calculator 121a calculates aberration information of the ocular optical system of the subject's eye E based on the morphology of the images of the returning light acquired by the area sensor 76a. For example, the storage unit 112 stores in advance data corresponding to the reference morphology corresponding to the Hartmann plate 75a. The aberration calculator 121a obtains, from the area sensor 76a, data of the images of the returning light acquired by the area sensor 76a. The aberration calculator 121a compares the morphology of the images of the returning light with the reference morphology based on the data of the images of the returning light and the data corresponding to the reference morphology stored in advance in the storage unit 112. Thereby, the aberration calculator 121a calculates aberration information for setting the subject's eye E to the same state as a normal vision. In this manner, the wavefront measurement optical system 7a and the aberration calculator 121a can acquire the aberration information of the ocular optical system of the subject's eye E. The wavefront measurement optical system 7a and the aberration calculator 121a are an example of an "aberration measurement unit" according to the present embodiment. The "aberration measurement unit" may further include a projection system of projecting measurement light of the interference optical system 14.

(Actions and Effects)

The actions and effects of the ophthalmic apparatus 1000a according to the embodiment will be described.

In the ophthalmic apparatus, the aberration measurement unit (for example, the wavefront measurement optical system 7a and the aberration calculator 121a) includes a Hartmann plate (for example, the Hartmann plate 75a), an area sensor (for example, the area sensor 76a), an aberration calculator (for example, the aberration calculator 121a). The Hartmann plate is provided in the optical path of the returning light from the subject's eye. The area sensor detects the returning light that has passed through the Hartmann plate. The aberration calculator compares the morphology of the images of the returning light acquired by the area sensor and the reference morphology based on the Hartmann plate so as to calculate aberration information.

According to such a configuration, it is possible to obtain up to high order aberration on the aberration information of the ocular optical system of the subject's eye E.

(Other Modifications)

The embodiment described above is only an example for carrying out the present invention. Those who intend to practice the present invention can apply any modification, omission, addition, etc. within the scope of the substance of the present invention.

In the above embodiment, the eyeball information calculator mainly calculates the axial length. However, the eyeball information calculator according to embodiments is not limited thereto. The eyeball information calculator may also calculate any of the corneal thickness, the anterior chamber depth, and the crystalline lens thickness in a similar way.

Optical elements and arrangement thereof are not limited to those described in the above embodiments. For example, instead of the half mirror in the above embodiments, a beam splitter may be provided.

It is possible to apply the invention according to the above embodiments to apparatuses having arbitrary functions adaptable in the field of ophthalmology. Examples of such functions include a tonometry function, a fundus photography function, an anterior segment photography function, an optical coherence tomography (OCT) function, an ultrasonic examination function, and the like. The tonometry function is realized by a tonometer or the like. The fundus photography function is realized by a fundus camera, a scanning laser ophthalmoscope (SLO) or the like. The anterior segment photography function is realized by a slit lamp microscope or the like. The OCT function is realized by an optical coherence tomography apparatus or the like. The ultrasonic examination function is realized by an ultrasonic diagnostic apparatus or the like. Further, the present invention can also be applied to an apparatus (multifunctional apparatus) having two or more of such functions.

Further, in a system to which the first embodiment and the second embodiment both can be applied, it is possible to selectively apply a desired embodiment of the two embodiments by switching operation modes.

The invention claimed is:

1. An ophthalmic apparatus comprising:
   a refractive power measurement unit configured to project light from a light source onto a subject's eye and detect returning light thereof to determine refractive power of an ocular optical system of the subject's eye; and
   an eyeball information measurement unit configured to project light from the light source onto the subject's eye and detect returning light thereof to determine eyeball information representing structure of the subject's eye.

2. The ophthalmic apparatus of claim 1, wherein part of an optical path of the light from the light source formed by the refractive power measurement unit and part of an optical path of the light from the light source formed by the eyeball information measurement unit are common.

3. The ophthalmic apparatus of claim 1, wherein the refractive power measurement unit comprises:
   a projection system configured to project the light from the light source onto a fundus of the subject's eye through a pupil center of or through an optical center of an eyeball of the subject's eye,
   a light reception system configured to receive light that has passed through a peripheral portion that is apart from the pupil center of or from the optical center of the eyeball of the subject's eye by a predetermined distance, among light reflected from the fundus, and
   a decentered member provided at a position substantially conjugate with a pupil of the subject's eye in a common optical path of the projection system and the light reception system.

4. The ophthalmic apparatus of claim 3, wherein the light reception system comprises a wedge prism configured to detect a light source image projected on the fundus as a plurality of point images that has passed through the peripheral portion.

5. The ophthalmic apparatus of claim 3, wherein the light reception system comprises a conical prism configured to detect a light source image projected on the fundus as a ring pattern that has passed through the peripheral portion.

6. The ophthalmic apparatus of claim 1, wherein the eyeball information measurement unit comprises:
   an interference optical system configured to split the light from the light source into reference light and measurement light, to project the measurement light onto the subject's eye, and to detect interference light generated from returning light thereof and the reference light, and
   an eyeball information calculator configured to calculate the eyeball information based on a detection result of the interference light acquired by the interference optical system.

7. The ophthalmic apparatus of claim 6, wherein the eyeball information measurement unit comprises a splitting member configured to generate a plurality of pieces of reference light from the light from the light source and is configured to acquire the eyeball information from a detection result of interference light generated from reflected light of the measurement light from a plurality of positions of the subject's eye and the plurality of pieces of reference light.

8. The ophthalmic apparatus of claim 6, wherein the eyeball information calculator is configured to calculate at least one of axial length, corneal thickness, anterior chamber depth, and crystalline lens thickness as the eyeball information.

9. The ophthalmic apparatus of claim 1, further comprising:
   a power calculator configured to calculate power of an intraocular lens based on the refractive power determined by the refractive power measurement unit and on the eyeball information determined by the eyeball information measurement unit.

10. The ophthalmic apparatus of claim 1, further comprising:
    a corneal shape measurement unit configured to project predetermined pattern light onto a cornea of the subject's eye, and based on a detection result of returning light thereof, to determine a parameter representing a shape of the cornea.

11. The ophthalmic apparatus of claim 1, further comprising:
    a visual target projection unit configured to project a visual target for a visual acuity measurement onto the fundus of the subject's eye.

12. The ophthalmic apparatus of claim 1, wherein the light source is a low coherence light source whose center wavelength is a value within the range of 820 nm to 880 nm.

13. The ophthalmic apparatus of claim 2, wherein the refractive power measurement unit comprises:
    a projection system configured to project the light from the light source onto a fundus of the subject's eye through a pupil center of or through an optical center of an eyeball of the subject's eye;
    a light reception system configured to receive light that has passed through a peripheral portion that is apart from the pupil center of or from the optical center of the eyeball of the subject's eye by a predetermined distance, among light reflected from the fundus; and
    a decentered member provided at a position substantially conjugate with a pupil of the subject's eye in a common optical path of the projection system and the light reception system.

14. The ophthalmic apparatus of claim 6, wherein the eyeball information measurement unit comprises:
    an interference optical system configured to split the light from the light source into reference light and measurement light, to project the measurement light onto the subject's eye, and to detect interference light generated from returning light thereof and the reference light; and an eyeball information calculator configured to calculate the eyeball information based on a detection result of the interference light acquired by the interference optical system.

15. The ophthalmic apparatus of claim 3, wherein the eyeball information measurement unit comprises:

an interference optical system configured to split the light from the light source into reference light and measurement light, to project the measurement light onto the subject's eye, and to detect interference light generated from returning light thereof and the reference light; and an eyeball information calculator configured to calculate the eyeball information based on a detection result of the interference light acquired by the interference optical system.

16. The ophthalmic apparatus of claim 9 further comprising:

a power calculator configured to calculate power of an intraocular lens based on the refractive power determined by the refractive power measurement unit and on the eyeball information determined by the eyeball information measurement unit.

17. The ophthalmic apparatus of claim 3 further comprising:

a power calculator configured to calculate power of an intraocular lens based on the refractive power determined by the refractive power measurement unit and on the eyeball information determined by the eyeball information measurement unit.

18. The ophthalmic apparatus of claim 2 further comprising:

a corneal shape measurement unit configured to project predetermined pattern light onto a cornea of the subject's eye, and based on a detection result of returning light thereof, to determine a parameter representing a shape of the cornea.

19. The ophthalmic apparatus of claim 3 further comprising:

a corneal shape measurement unit configured to project predetermined pattern light onto a cornea of the subject's eye, and based on a detection result of returning light thereof, to determine a parameter representing a shape of the cornea.

20. The ophthalmic apparatus of claim 2, wherein the light source is a low coherence light source whose center wavelength is a value within the range of 820 nm to 880 nm.

* * * * *